(12) United States Patent
Kang et al.

(10) Patent No.: US 7,718,414 B2
(45) Date of Patent: May 18, 2010

(54) **MICROORGANISM OF *ENTEROBACTERIACAE* GENUS HABORING GENES ASSOCIATED WITH L-CARNITINE BIOSYNTHESIS AND METHOD OF PRODUCING L-CARNITINE USING THE MICROORGANISM**

(75) Inventors: Whan-Koo Kang, Daejeon (KR); Bheong-Uk Lee, Busan (KR); Young-Hoon Park, Seongnam (KR); Eun-Sung Koh, Suwon (KR); Jae-Yeong Ju, Seongnam (KR); Jin-Ho Lee, Yongin (KR); Hye-Won Kim, Seongnam (KR); Hye-Jin Choi, Seoul (KR)

(73) Assignee: CJ Cheiljedang Corp. (KR)

( * ) Notice: Subject to any disclaimer, the term of this patent is extended or adjusted under 35 U.S.C. 154(b) by 114 days.

(21) Appl. No.: 11/994,969

(22) PCT Filed: Jul. 7, 2006

(86) PCT No.: PCT/KR2006/002661
§ 371 (c)(1),
(2), (4) Date: Jan. 7, 2008

(87) PCT Pub. No.: WO2007/007987
PCT Pub. Date: Jan. 18, 2007

(65) Prior Publication Data
US 2008/0171368 A1 Jul. 17, 2008

(30) Foreign Application Priority Data
Jul. 7, 2005 (KR) .................. 10-2005-0061142

(51) Int. Cl.
*C12P 13/00* (2006.01)
*C12N 1/20* (2006.01)
(52) U.S. Cl. ..................... 435/252.3; 435/252.33; 435/128
(58) Field of Classification Search ............... None
See application file for complete search history.

(56) References Cited

U.S. PATENT DOCUMENTS

| 4,221,869 A | 9/1980 | Vandecasteele et al. |
| 4,371,618 A | 2/1983 | Cavazza |
| 4,650,759 A | 3/1987 | Yokozeki et al. |
| 4,708,936 A | 11/1987 | Kulla et al. |
| 5,028,538 A | 7/1991 | Seim et al. |

FOREIGN PATENT DOCUMENTS

| DE | 3123975 | | 6/1981 |
| JP | 62118899 | | 5/1987 |
| WO | 2007007986 A1 | | 1/2007 |
| WO | WO 2007/011087 | * | 1/2007 |

OTHER PUBLICATIONS

Borum et al. JBC 1977, 252 pp. 5651-5655.*
Sambrook et al Molecular cloning A laboratory Manual 2nd ED 1989, pp. 8.46-8.52, 11.2-11.19.*
International Search Report for corresponding International Application No. PCT/KR2006/002661 dated Aug. 25, 2006.
Written Opinion of the International Searching Authority for corresponding International Application No. PCT/KR2006/002661 dated Aug. 25, 2006.
Borum, et al., "Purification of S-adenosylmethionine: epsilon-N-L-Lysine Methyltransferase," The Journal of Biological Chemistry, 252(16), 5651-5655 (1977).
European Search Report for 06769203.8—1212/1904620 dated Sep. 9, 2009.
Galagan, et al., "The genome sequence of filamentous fungus *Neurospora crassa*," Nature, 422(6934), 859-868 (2003).
McClung, et al., "Characterization of the Formate (for) Locus, Which Encodes the Cytosolic Serine Hydroxymethyltransferase of *Neurospora crassa*," Molecular and Cellular Biology, 12(4), 1412-1421 (1992).
Sweigers, et al., "Carnitine biosynthesis in *Neurospora crassa*: identification of a cDNA coding for epsilon-N-trimethyllysine hydroxylase and its functional expression in *Saccharomyces cerevisiae*," FEMS Microbiology Letters, 210, 19-23 (2002).
XP-002541633 retrieved from EBI accession No. Q7S7R7 (Dec. 15, 2003).
XP-002541634 retrieved from EBI accession No. Q96UB1 (Jun. 20, 2002).
XP-002541635 retrieved from EBI accession No. P34898 (Feb. 1, 1994).
XP-002541636 retrieved from EBI accession No. Q7RYT1 (Dec. 15, 2003).
XP-002541637 retrieved from EBI accession No. Q7S4C5 (Dec. 15, 2003).

* cited by examiner

*Primary Examiner*—Delia M Ramirez
*Assistant Examiner*—Md. Younus Meah
(74) *Attorney, Agent, or Firm*—Cantor Colburn LLP

(57) ABSTRACT

Provided is a microorganism that belongs to Enterobacteriacae and a method of producing L-carnitine using the same. The microorganism includes polynucleotide encoding activity of S-adenosylmethionine-6-N-lysine methyltransferase from Neurospora crassa, polynucleotide encoding activity of 6-N-trimethyllysine hydroxylase, polynucleotide encoding activity of 3-hydroxy-6-N-trimethyllysine aldolase, and polynucleotide encoding activity of γ-trimethylaminoaldehyde dehydrogenase and γ-butyrobetaine hydroxylase.

5 Claims, 13 Drawing Sheets

SEQUENCE LISTING

<160> NUMBER OF SEQ ID NOS: 21

<210> SEQ ID NO 1
<211> LENGTH: 33
<212> TYPE: DNA
<213> ORGANISM: Artificial Sequence
<220> FEATURE:
<223> OTHER INFORMATION: primer

<400> SEQUENCE: 1
ggaattccat atggccttcg gaaagcttta cac                    33

<210> SEQ ID NO 2
<211> LENGTH: 30
<212> TYPE: DNA
<213> ORGANISM: Artificial Sequence
<220> FEATURE:
<223> OTHER INFORMATION: primer

<400> SEQUENCE: 2
cgggatcctt agacgttggt caacttgggg                        30

<210> SEQ ID NO 3
<211> LENGTH: 32
<212> TYPE: DNA
<213> ORGANISM: Artificial Sequence
<220> FEATURE:
<223> OTHER INFORMATION: primer

<400> SEQUENCE: 3
atgaattcca tatgagaccg caagtggtag gg      32

<210> SEQ ID NO 4
<211> LENGTH: 32
<212> TYPE: DNA
<213> ORGANISM: Artificial Sequence
<220> FEATURE:
<223> OTHER INFORMATION: primer

<400> SEQUENCE: 4
atgaattctc attttccgct ggtttctttc cg      32

<210> SEQ ID NO 5
<211> LENGTH: 29
<212> TYPE: DNA
<213> ORGANISM: Artificial Sequence
<220> FEATURE:
<223> OTHER INFORMATION: primer

<400> SEQUENCE: 5
atggatccta atacgactca ctataggga      29

<210> SEQ ID NO 6
<211> LENGTH: 30
<212> TYPE: DNA
<213> ORGANISM: Artificial Sequence
<220> FEATURE:
<223> OTHER INFORMATION: primer

<400> SEQUENCE: 6
attaagcttt tagagaccgg catcgtatct      30

<210> SEQ ID NO 7
<211> LENGTH: 29
<212> TYPE: DNA
<213> ORGANISM: Artificial Sequence
<220> FEATURE:
<223> OTHER INFORMATION: primer

<400> SEQUENCE: 7
atggatccta atacgactca ctataggga      29

<210> SEQ ID NO 8
<211> LENGTH: 33
<212> TYPE: DNA
<213> ORGANISM: Artificial Sequence
<220> FEATURE:
<223> OTHER INFORMATION: primer

<400> SEQUENCE: 8
attgtcgact catgccgcca ggtttacatg gat      33

<210> SEQ ID NO 9
<211> LENGTH: 29
<212> TYPE: DNA
<213> ORGANISM: Artificial Sequence
<220> FEATURE:
<223> OTHER INFORMATION: primer

<400> SEQUENCE: 9
atggatccta atacgactca ctataggga      29

<210> SEQ ID NO 10
<211> LENGTH: 31
<212> TYPE: DNA

-continued

```
<213> ORGANISM: Artificial Sequence
<220> FEATURE:
<223> OTHER INFORMATION: primer

<400> SEQUENCE: 10
attagtcgac tcaataccct cccccaccct g                                      31

<210> SEQ ID NO 11
<211> LENGTH: 216
<212> TYPE: PRT
<213> ORGANISM: Neurospora crassa

<400> SEQUENCE: 11
```

Met Ala Phe Gly Lys Leu Tyr Thr Tyr Glu Ala Asn Pro Arg Ser Thr
 1               5                  10                  15

Ala Ile Leu Ala Val Ala Lys Ala Asn Asn Leu Asp Leu Glu Val Ile
             20                  25                  30

Lys Val Asp Leu Glu Ala Ala Ile Glu Glu Tyr Lys Lys Val Asn Pro
         35                  40                  45

Leu Gly Lys Val Pro Thr Phe Val Gly Ala Asp Gly Tyr Thr Leu Phe
     50                  55                  60

Glu Cys Ile Ala Ile Ala Ile Tyr Val Ala Ser Gln Asn Glu Lys Thr
 65                  70                  75                  80

Thr Leu Leu Gly Lys Thr Lys Gln Asp Tyr Ala Ser Ile Leu Lys Trp
                 85                  90                  95

Leu Ser Phe Phe Asn Thr Glu Val Leu Pro Pro Leu Ala Gly Trp Tyr
            100                 105                 110

Arg Pro Leu Leu Gly Lys Ala Pro Tyr Asn Lys Lys Ala Val Glu Asp
        115                 120                 125

Ala Gln Ala Thr Ala Leu Lys Ala Ile Ser Val Ala Glu Ala His Leu
    130                 135                 140

Lys Asn Asn Thr Phe Pro Val Gly Glu Arg Ile Thr Leu Ala Asp Leu
145                 150                 155                 160

Phe Ala Thr Gly Ile Ile Ala Arg Gly Phe Glu Phe Phe Asp Lys
                165                 170                 175

Ala Trp Arg Glu Gln Tyr Pro Asn Val Thr Arg Trp Tyr Thr Thr Val
            180                 185                 190

Tyr Asn Gln Pro Ile Tyr Ser Ala Val Ala Pro Phe Ala Leu Leu
        195                 200                 205

Asp Thr Pro Lys Leu Thr Asn Val
    210                 215

```
<210> SEQ ID NO 12
<211> LENGTH: 471
<212> TYPE: PRT
<213> ORGANISM: Neurospora crassa

<400> SEQUENCE: 12
```

Met Arg Pro Gln Val Val Gly Ala Ile Leu Arg Ser Arg Ala Val Val
 1               5                  10                  15

Ser Arg Gln Pro Leu Ser Arg Thr His Ile Phe Ala Ala Val Thr Val
             20                  25                  30

Ala Lys Ser Ser Ser Pro Ala Gln Asn Ser Arg Arg Thr Phe Ser Ser
         35                  40                  45

Ser Phe Arg Arg Leu Tyr Glu Pro Lys Ala Glu Ile Thr Ala Glu Gly
     50                  55                  60

Leu Glu Leu Ser Pro Pro Gln Ala Val Thr Gly Gly Lys Arg Thr Val

```
                65                  70                  75                  80
Leu Pro Asn Phe Trp Leu Arg Asp Asn Cys Arg Cys Thr Lys Cys Val
                        85                  90                  95

Asn Gln Asp Thr Leu Gln Arg Asn Phe Asn Thr Phe Ala Ile Pro Ser
            100                 105                 110

Asp Ile His Pro Thr Lys Val Glu Ala Thr Lys Glu Asn Val Thr Val
            115                 120                 125

Gln Trp Ser Asp Asn His Thr Ser Thr Tyr Pro Trp Pro Phe Leu Ser
    130                 135                 140

Phe Tyr Leu Thr Ser Asn Ala Arg Gly His Glu Asn Asp Gln Ile Ser
145                 150                 155                 160

Leu Trp Gly Ser Glu Ala Gly Ser Arg Pro Thr Val Pro Phe Pro
                165                 170                 175

Arg Val Met Ala Ser Asp Gln Gly Val Ala Asp Leu Thr Ala Met Ile
            180                 185                 190

Lys Glu Phe Gly Phe Cys Phe Val Lys Asp Thr Pro His Asp Asp Pro
                195                 200                 205

Asp Val Thr Arg Gln Leu Leu Glu Arg Ile Ala Phe Ile Arg Val Thr
            210                 215                 220

His Tyr Gly Gly Phe Tyr Asp Phe Thr Pro Asp Leu Ala Met Ala Asp
225                 230                 235                 240

Thr Ala Tyr Thr Asn Leu Ala Leu Pro Ala His Thr Asp Thr Thr Tyr
                    245                 250                 255

Phe Thr Asp Pro Ala Gly Leu Gln Ala Phe His Leu Leu Glu His Lys
                260                 265                 270

Ala Ala Pro Ser Arg Pro Pro Pro Pro Pro Pro Pro Pro Pro Pro Pro
            275                 280                 285

Ser Glu Glu Lys Glu Ala Ala Gly Ser Ala Ala Gly Glu Ala Ala Ala
    290                 295                 300

Ala Ala Glu Gly Gly Lys Ser Leu Leu Val Asp Gly Phe Asn Ala Ala
305                 310                 315                 320

Arg Ile Leu Lys Glu Glu Asp Pro Arg Ala Tyr Glu Ile Leu Ser Ser
                325                 330                 335

Val Arg Leu Pro Trp His Ala Ser Gly Asn Glu Gly Ile Thr Ile Ala
                340                 345                 350

Pro Asp Lys Leu Tyr Pro Val Leu Glu Leu Asn Glu Asp Thr Gly Glu
            355                 360                 365

Leu His Arg Val Arg Trp Asn Asn Asp Asp Arg Gly Val Val Pro Phe
            370                 375                 380

Gly Glu Lys Tyr Ser Pro Ser Glu Trp Tyr Glu Ala Ala Arg Lys Trp
385                 390                 395                 400

Asp Gly Ile Leu Arg Arg Lys Ser Ser Glu Leu Trp Val Gln Leu Glu
                    405                 410                 415

Pro Gly Lys Pro Leu Ile Phe Asp Asn Trp Arg Val Leu His Gly Arg
                420                 425                 430

Ser Ala Phe Ser Gly Ile Arg Arg Ile Cys Gly Gly Tyr Ile Asn Arg
            435                 440                 445

Asp Asp Phe Ile Ser Arg Trp Arg Asn Thr Asn Tyr Pro Arg Ser Glu
            450                 455                 460

Val Leu Pro Arg Val Thr Gly
465                 470

<210> SEQ ID NO 13
```

<211> LENGTH: 480
<212> TYPE: PRT
<213> ORGANISM: Neurospora crassa

<400> SEQUENCE: 13

```
Met Ser Thr Tyr Ser Leu Ser Glu Thr His Lys Ala Met Leu Glu His
  1               5                  10                  15

Ser Leu Val Glu Ser Asp Pro Gln Val Ala Glu Ile Met Lys Lys Glu
             20                  25                  30

Val Gln Arg Gln Arg Glu Ser Ile Ile Leu Ile Ala Ser Glu Asn Val
         35                  40                  45

Thr Ser Arg Ala Val Phe Asp Ala Leu Gly Ser Pro Met Ser Asn Lys
     50                  55                  60

Tyr Ser Glu Gly Leu Pro Gly Ala Arg Tyr Tyr Gly Gly Asn Gln His
 65                  70                  75                  80

Ile Asp Glu Ile Glu Val Leu Cys Gln Asn Arg Ala Leu Glu Ala Phe
                 85                  90                  95

His Leu Asp Pro Lys Gln Trp Gly Val Asn Val Gln Cys Leu Ser Gly
            100                 105                 110

Ser Pro Ala Asn Leu Gln Val Tyr Gln Ala Ile Met Pro Val His Gly
        115                 120                 125

Arg Leu Met Gly Leu Asp Leu Pro His Gly Gly His Leu Ser His Gly
    130                 135                 140

Tyr Gln Thr Pro Gln Arg Lys Ile Ser Ala Val Ser Thr Tyr Phe Glu
145                 150                 155                 160

Thr Met Pro Tyr Arg Val Asn Ile Asp Thr Gly Leu Ile Asp Tyr Asp
                165                 170                 175

Thr Leu Glu Lys Asn Ala Gln Leu Phe Arg Pro Lys Val Leu Val Ala
            180                 185                 190

Gly Thr Ser Ala Tyr Cys Arg Leu Ile Asp Tyr Glu Arg Met Arg Lys
        195                 200                 205

Ile Ala Asp Ser Val Gly Ala Tyr Leu Val Val Asp Met Ala His Ile
    210                 215                 220

Ser Gly Leu Ile Ala Ser Glu Val Ile Pro Ser Pro Phe Leu Tyr Ala
225                 230                 235                 240

Asp Val Val Thr Thr Thr His Lys Ser Leu Arg Gly Pro Arg Gly
                245                 250                 255

Ala Met Ile Phe Phe Arg Arg Gly Val Arg Ser Val Asp Ala Lys Thr
            260                 265                 270

Gly Lys Glu Thr Leu Tyr Asp Leu Glu Asp Lys Ile Asn Phe Ser Val
        275                 280                 285

Phe Pro Gly His Gln Gly Gly Pro His Asn His Thr Ile Thr Ala Leu
    290                 295                 300

Ala Val Ala Leu Lys Gln Ala Ala Ser Pro Glu Phe Lys Glu Tyr Gln
305                 310                 315                 320

Gln Lys Val Val Ala Asn Ala Lys Ala Leu Glu Lys Leu Lys Glu
                325                 330                 335

Leu Gly Tyr Lys Leu Val Ser Asp Gly Thr Asp Ser His Met Val Leu
            340                 345                 350

Val Asp Leu Arg Pro Ile Gly Val Asp Gly Ala Arg Val Glu Phe Leu
        355                 360                 365

Leu Glu Gln Ile Asn Ile Thr Cys Asn Lys Asn Ala Val Pro Gly Asp
    370                 375                 380

Lys Ser Ala Leu Thr Pro Gly Gly Leu Arg Ile Gly Thr Pro Ala Met
```

-continued

```
            385                 390                 395                 400
Thr Ser Arg Gly Phe Gly Glu Ala Asp Phe Glu Lys Val Ala Val Phe
                405                 410                 415

Val Asp Glu Ala Val Lys Leu Cys Lys Glu Ile Gln Ala Ser Leu Pro
            420                 425                 430

Lys Glu Ala Asn Lys Gln Lys Asp Phe Lys Ala Lys Ile Ala Thr Ser
            435                 440                 445

Asp Ile Pro Arg Ile Asn Glu Leu Lys Gln Glu Ile Ala Ala Trp Ser
        450                 455                 460

Asn Thr Phe Pro Leu Pro Val Glu Gly Trp Arg Tyr Asp Ala Gly Leu
465                 470                 475                 480

<210> SEQ ID NO 14
<211> LENGTH: 495
<212> TYPE: PRT
<213> ORGANISM: Neurospora crassa

<400> SEQUENCE: 14

Met Glu Val Glu Leu Thr Ala Pro Asn Gly Lys Lys Trp Met Gln Pro
  1               5                  10                  15

Leu Gly Leu Phe Ile Asn Asn Glu Phe Val Lys Ser Ala Asn Glu Gln
                 20                  25                  30

Lys Leu Ile Ser Ile Asn Pro Thr Thr Glu Glu Ile Cys Ser Val
             35                  40                  45

Tyr Ala Ala Thr Ala Glu Asp Val Asp Ala Val Ser Ala Ala Arg
         50                  55                  60

Lys Ala Phe Arg His Glu Ser Trp Lys Ser Leu Ser Gly Thr Glu Arg
 65                  70                  75                  80

Gly Ala Leu Met Arg Lys Leu Ala Asp Leu Val Ala Glu Asn Ala Glu
                 85                  90                  95

Ile Leu Ala Thr Ile Glu Cys Leu Asp Asn Gly Lys Pro Tyr Gln Thr
            100                 105                 110

Ala Leu Asn Glu Asn Val Pro Glu Val Ile Asn Val Leu Arg Tyr Tyr
        115                 120                 125

Ala Gly Tyr Ala Asp Lys Asn Phe Gly Gln Val Ile Asp Val Gly Pro
    130                 135                 140

Ala Lys Phe Ala Tyr Thr Val Lys Glu Pro Leu Gly Val Cys Gly Gln
145                 150                 155                 160

Ile Ile Pro Trp Asn Tyr Pro Leu Asp Met Ala Ala Trp Lys Leu Gly
                165                 170                 175

Pro Ala Leu Cys Cys Gly Asn Thr Val Val Leu Lys Leu Ala Glu Gln
            180                 185                 190

Thr Pro Leu Ser Val Leu Tyr Leu Ala Lys Leu Ile Lys Glu Ala Gly
        195                 200                 205

Phe Pro Pro Gly Val Ile Asn Ile Ile Asn Gly His Gly Arg Glu Ala
    210                 215                 220

Gly Ala Ala Leu Val Gln His Pro Gln Val Asp Lys Ile Ala Phe Thr
225                 230                 235                 240

Gly Ser Thr Thr Thr Gly Lys Glu Ile Met Lys Met Ala Ser Tyr Thr
                245                 250                 255

Met Lys Asn Ile Thr Leu Glu Thr Gly Gly Lys Ser Pro Leu Ile Val
            260                 265                 270

Phe Glu Asp Ala Asp Leu Glu Leu Ala Ala Thr Trp Ser His Ile Gly
        275                 280                 285
```

```
Ile Met Ser Asn Gln Gly Gln Ile Cys Thr Ala Thr Ser Arg Ile Leu
    290                 295                 300

Val His Glu Lys Ile Tyr Asp Glu Phe Val Glu Lys Phe Lys Ala Lys
305                 310                 315                 320

Val Gln Glu Val Ser Val Leu Gly Asp Pro Phe Glu Glu Ser Thr Phe
                325                 330                 335

His Gly Pro Gln Val Thr Lys Ala Gln Tyr Glu Arg Val Leu Gly Tyr
            340                 345                 350

Ile Asn Val Gly Lys Glu Gly Ala Thr Val Met Met Gly Gly Glu
        355                 360                 365

Pro Ala Pro Gln Asn Gly Lys Gly Phe Phe Val Ala Pro Thr Val Phe
370                 375                 380

Thr Asn Val Lys Pro Thr Met Lys Ile Phe Arg Glu Glu Ile Phe Gly
385                 390                 395                 400

Pro Cys Val Ala Ile Thr Thr Phe Lys Thr Glu Glu Glu Ala Leu Thr
                405                 410                 415

Leu Ala Asn Asp Ser Met Tyr Gly Leu Gly Ala Ala Leu Phe Thr Lys
            420                 425                 430

Asp Leu Thr Arg Ala His Arg Val Ala Arg Glu Ile Glu Ala Gly Met
        435                 440                 445

Val Trp Val Asn Ser Ser Asn Asp Ser Asp Phe Arg Ile Pro Phe Gly
450                 455                 460

Gly Val Lys Gln Ser Gly Ile Gly Arg Glu Leu Gly Glu Ala Gly Leu
465                 470                 475                 480

Ala Pro Tyr Cys Asn Val Lys Ser Ile His Val Asn Leu Ala Ala
                485                 490                 495

<210> SEQ ID NO 15
<211> LENGTH: 425
<212> TYPE: PRT
<213> ORGANISM: Neurospora crassa

<400> SEQUENCE: 15

Met Ala Thr Ala Ala Val Gln Val Ser Val Pro Ala Pro Val Gly Gln
1               5                   10                  15

Pro Asp Ile Gly Tyr Ala Pro Asp His Asp Lys Tyr Leu Ala Arg Val
            20                  25                  30

Lys Arg Arg Arg Glu Asn Glu Lys Leu Glu Ser Ser Leu Pro Pro Gly
        35                  40                  45

Phe Pro Arg Arg Leu Asp Ser Asp Leu Val Trp Asp Gly Asn Thr Leu
50                  55                  60

Ala Glu Thr Tyr Asp Trp Thr Tyr Arg Leu Thr Glu Glu Ala Ile Asp
65                  70                  75                  80

Glu Ile Glu Ala Ala Leu Arg His Phe Lys Ser Leu Asn Lys Pro Leu
                85                  90                  95

Gly Tyr Ile Asn Gln Glu Thr Phe Pro Leu Pro Arg Leu His His Thr
            100                 105                 110

Leu Arg Ser Leu Ser His Glu Leu His His Gly His Gly Phe Lys Val
        115                 120                 125

Leu Arg Gly Leu Pro Val Thr Ser His Thr Arg Glu Glu Asn Ile Ile
130                 135                 140

Ile Tyr Ala Gly Val Ser Ser His Val Ala Pro Ile Arg Gly Arg Gln
145                 150                 155                 160

Asp Asn Gln His Asn Gly His Pro Ala Asp Val Val Leu Ala His Ile
                165                 170                 175
```

```
Lys Asp Leu Ser Thr Thr Val Ser Asp Val Ser Lys Ile Gly Ala Pro
        180                 185                 190
Ala Tyr Thr Thr Glu Lys Gln Val Phe His Thr Asp Ala Gly Asp Ile
        195                 200                 205
Val Ala Leu Phe Cys Leu Gly Glu Ala Ala Glu Gly Gly Gln Ser Tyr
        210                 215                 220
Leu Ser Ser Ser Trp Lys Val Tyr Asn Glu Leu Ala Ala Thr Arg Pro
225                 230                 235                 240
Asp Leu Val Arg Thr Leu Ala Glu Pro Trp Val Ala Asp Glu Phe Gly
                245                 250                 255
Lys Glu Gly Arg Lys Phe Ser Val Arg Pro Leu Leu His Phe Gln Ser
        260                 265                 270
Thr Ala Ala Ala Ser Arg Glu Ala Lys Pro Glu Ser Glu Arg Leu
        275                 280                 285
Ile Ile Gln Tyr Ala Arg Arg Thr Phe Thr Gly Tyr Trp Gly Leu Pro
        290                 295                 300
Arg Ser Ala Asp Ile Pro Pro Ile Thr Glu Ala Gln Ala Glu Ala Leu
305                 310                 315                 320
Asp Ala Leu His Phe Thr Ala Glu Lys Tyr Ala Val Ala Leu Asp Phe
                325                 330                 335
Arg Gln Gly Asp Val Gln Phe Val Asn Asn Leu Ser Val Phe His Ser
        340                 345                 350
Arg Ala Gly Phe Arg Asp Glu Gly Glu Lys Gln Arg His Leu Val Arg
        355                 360                 365
Leu Trp Leu Arg Asp Pro Glu Asn Ala Trp Glu Thr Pro Glu Ala Leu
        370                 375                 380
Lys Glu Arg Trp Glu Arg Val Tyr Gly Gly Val Ser Pro Glu Arg Glu
385                 390                 395                 400
Val Phe Pro Leu Glu Pro Gln Ile Arg Ser Ala Ser Lys Gly Glu Ser
                405                 410                 415
Val Gly Thr Gln Gly Gly Gly Gly Tyr
        420                 425

<210> SEQ ID NO 16
<211> LENGTH: 651
<212> TYPE: DNA
<213> ORGANISM: Neurospora crassa

<400> SEQUENCE: 16
atggccttcg gaaagcttta cacctacgag gcgaaccccc gctccacggc catcttggct      60
gtcgcgaagg ccaacaacct cgacctcgag gttatcaagg tcgaccttga ggctgccatc     120
gaggagtaca agaaggtcaa ccctctcggc aaggtcccca ccttcgttgg tgccgacggc     180
tacactctct tcgagtgcat cgccatcgcc atctatgtcg cttcccagaa cgagaagacc     240
actctcctcg gcaagaccaa gcaggactat gcctccatcc tgaagtggct ctctttcttc     300
aacaccgagg tccttccccc tcttgctggc tggtaccgcc ctctccttgg caaggctccc     360
tacaacaaga aggctgttga ggacgctcag gctactgccc tcaaggccat ctctgtcgcc     420
gaggcccacc tcaagaacaa caccttcccc gttggcgagc gcatcaccct tgccgatctc     480
ttcgccactg gcatcattgc ccgcggcttc gagttcttct cgacaaggc ctggcgcgag     540
cagtacccca cgtcacccg ttggtacacc actgtctaca accagcccat ctactcggcc     600
gttgctcctc ccttcgctct ccttgatacc cccaagttga ccaacgtcta a             651
```

<210> SEQ ID NO 17
<211> LENGTH: 1407
<212> TYPE: DNA
<213> ORGANISM: Neurospora crassa

<400> SEQUENCE: 17

| | | | | | |
|---|---|---|---|---|---|
| atgagaccgc | aagtggtagg | ggcaatcctc | cgctctagag | ctgttgtcag | cagacaacct | 60 |
| ctttcgagga | cccatatctt | tgctgccgtc | actgttgcaa | agtcctcatc | acctgcccag | 120 |
| aactcgagaa | gaaccttttc | atcctctttc | cgacggttgt | atgagccaaa | ggcggagata | 180 |
| acagctgagg | gacttgagtt | gagccctcca | caggctgtta | cgggtggaaa | gcggactgtt | 240 |
| ttacccaact | tctggctacg | tgacaactgc | cggtgtacga | aatgcgtgaa | ccaagatact | 300 |
| ctccagagaa | acttcaacac | ttttgccatc | ccctccgaca | tccacccaac | aaaggttgaa | 360 |
| gccaccaagg | agaacgtcac | cgtccaatgg | tccgacaacc | acacatccac | ctaccctgg | 420 |
| cccttcctct | ctttctacct | cacctccaac | gcgcgcgggc | acgaaaacga | ccagatctcc | 480 |
| ctctggggct | ccgaagccgg | ctcccgcccg | ccaaccgtct | ccttccctcg | cgtgatggca | 540 |
| tcagaccagg | gcgtcgccga | cctaaccgcc | atgatcaaag | agttcggctt | ctgtttcgtc | 600 |
| aaagacacac | cccatgacga | cccggacgtg | accgccagc | ttctggagag | aatcgccttt | 660 |
| atccgagtga | cccattacgg | cggcttttac | gatttcacgc | ccgacctcgc | gatggccgac | 720 |
| acggcgtaca | cgaacctggc | gctgccggcg | catacggata | cgacgtactt | cacggacccg | 780 |
| gcggggttgc | aggcttttca | cttgttggag | cataaggccg | ctccttctcg | tcctcctcct | 840 |
| cctcctcctc | ctcctcctcc | tccttctgaa | gaaaagaag | ctgcaggctc | agcagcaggg | 900 |
| gaggcggcgg | cggcagcaga | agggggaaag | tcgttgttgg | tcgatgggtt | caacgccgcg | 960 |
| aggattctga | aggaggagga | tccccgggct | tatgagatct | tgagcagcgt | gagactgccg | 1020 |
| tggcatgcga | gtgaaacga | agggatcacg | attgcgcccg | ataagcttta | tccggtgctg | 1080 |
| gaactgaatg | aggataccgg | ggaactgcat | agggttaggt | ggaataatga | tgatagggt | 1140 |
| gtggtgccgt | ttggggagaa | gtacagcccg | tcagagtggt | atgaggcggc | gaggaagtgg | 1200 |
| gatgggattt | tgaggaggaa | gagcagcgag | ttgtgggtgc | agttggagcc | ggggaagccg | 1260 |
| ttgaggttct | tcatgacgg | agcgcgttct | cgggtattag | gaggatttgt | ggagggtata | 1320 |
| tcaaccgcga | tgacttcatc | tctcggtgga | ggaacacgaa | ttacccaagg | agcgaggttc | 1380 |
| ttccgagggt | tactggttaa | ggactga | | | | 1407 |

<210> SEQ ID NO 18
<211> LENGTH: 1443
<212> TYPE: DNA
<213> ORGANISM: Neurospora crassa

<400> SEQUENCE: 18

| | | | | | |
|---|---|---|---|---|---|
| atgtctacct | actccctctc | cgagactcac | aaggccatgc | tcgagcatag | cttggtcgag | 60 |
| tccgaccccc | aggtcgccga | gatcatgaag | aaggaggttc | agcgccagcg | cgagtccatc | 120 |
| atcctcatcg | cctccgagaa | cgtcacctcg | cgtgccgtct | tcgatgccct | cggctccccc | 180 |
| atgtccaaca | agtactcgga | gggtcttccc | ggcgcccgct | actatggtgg | caaccagcac | 240 |
| atcgacgaga | tcgaggttct | ctgccagaac | cgtgcccttg | aggccttcca | cctcgacccc | 300 |
| aagcagtggg | gtgtcaatgt | tcagtgcttg | tccggcagcc | ctgccaacct | ccaggtctac | 360 |
| caggccatca | tgcccgtcca | cggcagactc | atgggtcttg | acctccccca | cggtggccat | 420 |
| ctttcccacg | gttaccagac | cccccagcgc | aagatctctg | ctgtctctac | ctacttcgag | 480 |

```
accatgccct accgcgtcaa cattgacact ggtctcatcg actacgatac cctcgagaag    540
aacgcccagc tcttccgccc aaggtcctc gtcgccggta cctctgccta ctgccgtctg    600
attgactacg agcgcatgcg caagattgcc gactccgttg gcgcttacct tgtcgtcgat    660
atggctcaca tttccggcct cattgcctcc gaggttatcc cctcgccctt cctctacgcc    720
gatgtcgtca ccaccaccac tcacaagtct ctccgtggcc ctcgtggcgc catgatcttc    780
ttccgccgcg gtgtccgctc cgttgacgcc aagaccggca aggagaccct ctacgacctt    840
gaggacaaga tcaacttctc cgtcttccct ggtcaccagg gtggccccca caaccacacc    900
atcaccgccc ttgccgttgc cctcaagcag gctgcctccc ccgagttcaa ggagtaccag    960
cagaaggtcg ttgccaacgc caaggctctc gagaagaagc tcaaggagct cggctacaag   1020
ctcgtctctg acggcactga ctctcacatg gtcctcgttg accttcgccc catcggcgtc   1080
gatggtgccc gtgttgagtt cctccttgag cagatcaaca ttacctgcaa caagaacgcc   1140
gttcccggcg acaagagcgc cctcaccccc ggcggtctcc gtattggtac cccgctatg   1200 acctcccgtg gcttcggcga ggccgacttc gagaaggtcg ccgtcttcgt cgatgaggct   1260
gtcaagctct gcaaggagat ccaggcttcc ctccccaagg aggctaacaa gcagaaggac   1320
ttcaaggcca agatcgccac cagcgatatt ccccgcatca acgagctcaa gcaggagatt   1380
gccgcctgga gcaacacctt ccccctcccc gttgagggct ggagatacga tgccggtctc   1440
taa                                                                 1443

<210> SEQ ID NO 19
<211> LENGTH: 1488
<212> TYPE: DNA
<213> ORGANISM: Neurospora crassa

<400> SEQUENCE: 19
atggaagtcg agcttacggc ccccaacggc aagaagtgga tgcagccact gggcttgttc     60
attaataacg agtttgtcaa aagtgccaat gagcagaagt tgatttccat caacccaact    120
accgaagagg agatctgctc ggtatacgcc gcaaccgccg aggatgttga cgccgcagta    180
tcagcagccc gcaaggcctt taggcacgaa tcatggaagt cgctatccgg cactgagcgc    240
ggcgccctga tgcgcaagct ggccgaccta gtggccgaga tgccgaaat cctagccacc    300 atcgagtgcc tggacaacgg caagccgtat cagacagccc ttaacgagaa cgtgcccgaa    360
gtgatcaacg tcctcaggta ctatgccggc tatgcggaca agaactttgg ccaagtgatt    420
gacgttggcc ccgccaagtt tgcctacacg gtcaaggagc ctctcggcgt atgtggccag    480
atcatcccct ggaactaccc gctagatatg gccgcctgga agctggggcc agctctctgc    540
tgcggcaaca ccgtggtcct caagctggcc gagcagactc ccctgtccgt gttgtacttg    600
gctaagctca ttaaggaggc cggcttccct cccggtgtga tcaatatcat caacggacac    660
ggcagggaag cgggtgccgc acttgtgcaa catcctcagg tggacaagat tgcctttacc    720
ggcagcacca ctacgggcaa ggagatcatg aagatggctt cctataccat gaagaacatc    780
accctggaga ctggcggcaa gtcaccgttg atcgtgtttg aggatgccga ccttgagctg    840
gcggcgacat ggtcacacat cggcatcatg agcaaccagg gccaaatctg cacagccact    900
tcacgcattc tcgtgcacga gaagatctac gacgagtttg tcgaaaaatt caaggccaaa    960
gtccaggagg tttcggtact cggcgacccc ttcgaggaga gcacgttcca cggacctcag   1020
gtcaccaaag cgcagtatga gcgtgttctg ggctatatca atgtcggaaa ggaagagggt   1080
```

```
gccacggtga tgatgggtgg tgagccggct ccgcagaacg gtaaaggttt ctttgtggcc      1140
ccgactgtct tcacgaacgt caagccgacc atgaagatct caggaggag gatctttggg       1200 ccctgcgtgg ccattaccac gttcaaaacg gaggaggagg cgttgacgct ggccaacgac      1260
agcatgtatg gcctgggagc ggctctgttc accaaggacc taaccaggc acacagagtg       1320 gcgcgggaga tcgaggccgg catggtctgg gtcaacagca gcaacgattc agactttagg      1380
attccatttg gaggcgtgaa gcagtctggt attgggaggg agttgggaga ggcaggtctg      1440
gcaccttatt gcaacgtcaa gagtatccat gtaaacctgg cggcatga                   1488
```

<210> SEQ ID NO 20
<211> LENGTH: 1278
<212> TYPE: DNA
<213> ORGANISM: Neurospora crassa

<400> SEQUENCE: 20

```
atggccacgg cagcggttca ggtttcagtc ccagctccgg ttggacaacc agatatcggg       60
tacgctcctg accacgacaa gtacctcgca agagtcaaaa gacgacgaga aaacgagaag      120
ctggagtcgt ctcttccgcc aggtttccct cgaagactag actcggacct tgtgtgggac      180
ggcaacaccc tcgccgagac gtacgactgg acctacagac tgacagaaga ggccattgat      240
gaaatcgagg ccgcgcttcg tcattttaag agcctcaaca gccccctagg ctacatcaac      300
caagaaacct tccccccttcc ccgcctacac cacactctcc gctccctctc ccacgagctc      360
caccacggcc acggcttcaa agtcctccgc gggctccccg tcacctccca tacacgcgag      420
gaaaacatca tcatctacgc cggcgtctcc tcgcatgtcg ctcctatccg cggccgccag      480
gacaaccagc acaacggcca cccagccgac gtagtcctag cacacatcaa agacctgtcc      540
acgactgttt ctgacgtgag caaaatcggt gcaccgcct acaccaccga gaaacaagtc       600
ttccacaccg acgcaggcga catcgtcgcc ctcttttgct gggagaggc cgccgagggc       660 ggacagagtt acctgtccag cagctggaag gtgtacaacg agctggcagc cactcggccc      720
gatctggttc gcacgctggc ggagccgtgg gtggcggacg agtttggcaa ggaagggagg      780
aagttttctg tgcgaccgct tttgcatttt cagtctactg ctgctgctgc ttctagggaa      840
gcaaagcccg agtctgaacg gctcatcatc cagtacgccc gccgcacgtt tacggggtat      900
tggggattac cgaggtcggc ggatatcccg cccattacgg aggcgcaggc ggaggcgttg      960
gatgcgctgc actttacggc ggagaagtac gcggtggcgc tggatttcag gcaggggat     1020 gtccagtttg tgaataactt gagtgtgttc cattcgaggg cggggtttag agatgagggg     1080
gagaagcaga ggcatttggt taggttgtgg ttgagagatc cggagaatgc gtgggagacg     1140
cccgaggcgt tgaaggaacg gtgggaacgc gtgtatggcg gggtgagtcc ggagagggag     1200
gtgtttccgc ttgagccgca gattaggagc gcgagtaagg gggagagcgt ggggacgcag     1260
ggtgggggag ggtattga                                                   1278
```

<210> SEQ ID NO 21
<211> LENGTH: 5
<212> TYPE: PRT
<213> ORGANISM: Neurospora crassa

<400> SEQUENCE: 21

Ala Phe Gly Lys Leu
 1               5

MICROORGANISM OF *ENTEROBACTERIACAE* GENUS HABORING GENES ASSOCIATED WITH L-CARNITINE BIOSYNTHESIS AND METHOD OF PRODUCING L-CARNITINE USING THE MICROORGANISM

TECHNICAL FIELD

The present invention relates to a microorganism of *Enterobacteriacae* including genes associated with biosynthesis of L-carnitine from *Neurospora crassa* and a method of producing L-carnitine using the microorganism.

BACKGROUND ART

L-carnitine(3-hydroxy-4-trimethylaminobutyrate) generally exists in organisms, and is a zwitterionic compound that carries long-chain activated fatty acids into the mitochondrial matrix across the inner mitochondrial membranes in the mitochondria. It is known that L-carnitine in the human body is synthesized from lysine or protein lysine. Generally, in a mammal, protein lysine is used as a precursor of L-carnitine biosynthesis, but free lysine is used in *Neurospora crassa*. In L-carnitine biosynthesis, ε-N,N,N-trimethyllysine, ε-N,N,N-trimethyl-β-hydroxyllysine, a N,N,N-trimethylamino butyraldehyde intermediate, and γ-butyrobetaine are produced, and γ-butyrobetaine is hydroxylated by γ-butyrobetaine hydroxylase to be L-carnitine. FIG. 1 is a flowchart illustrating a supposed biosynthetic pathway of L-carnitine in *Neurospora crassa*.

L-carnitine can be produced by a chemical synthesis method, a semi-synthesis method using an enzyme reaction, and a method of using a microorganism. However, when the chemical synthesis method is used, there is a problem in that a racemate of DL-carnitine is obtained, and thus this has to be separated. As an example of the semi-synthesis method using an enzyme reaction, U.S. Pat. No. 4,221,869 discloses a method of producing L-carnitine from dehydrocarnitine with carnitine dehydrogenase (EC 1.1.1.108) that uses NAD as a coenzyme. However, dehydrocarnitine is very unstable, and spontaneously decomposes into acetonyl trimethylammonium and carbon dioxide. In addition, DE Patent No. DE-OS-3123975 discloses a method of producing L-carnitine from γ-butyrobetaine with γ-butyrobetaine hydroxylase (EC 1.14.11.1) separated from *Neurospora crassa*. However, there is a disadvantage in that α-ketoglutarate and a reductant (that is, ascorbate) should be added to a reactant during hydroxylation.

As a method of producing L-carnitine using a microorganism, for example, U.S. Pat. No. 5,028,538 discloses a method of collecting L-carnitine from the culture obtained after *E. coli* 044 K 74 is cultured in a medium containing crotonobetaine (4-N,N,N-triethylamino crotonic acid). In addition, U.S. Pat. No. 4,708,936 discloses a method of producing L-carnitine culturing *Achromobacter xylosoxydans* DSM 3225 (HK 1331b) in a medium containing crotonobetain and/or γ-butyrobetaine. However, there are disadvantages in that a precursor of L-carnitine biosynthesis, such as crotonobetain, or a compound that is not an intermediate should be used, and production efficiency of L-carnitine is not high. Therefore, there still remains a need for improving production efficiency in a method of producing L-carnitine using a microorganism.

The inventors of the present invention have tried to produce a microorganism of L-carnitine that uses an inexpensive precursor and also has a high production efficiency, and have found that genes associated with L-carnitine biosynthesis derived from *Neurospora crassa* were well expressed in a microorganism of *Enterobacteriacae*, thereby completing the present invention.

DESCRIPTION OF THE DRAWINGS

In FIG. 12, lane 1 represents a marker, lane 2 represents pT7-7TMLH, lane 3 represents pT7-7TMLA, lane 4 represents pT7-7TMABADH and lane 5 represents pT7-7BBH.

In FIG. 13, lane 1 represents a marker, lane 2 represents a negative control group, lane 3 represents pT7-7TMLH (52 KDa), lane 4 represents pT7-7TMLA (53 KDa), lane 5 represents pT7-7TMABADH (55 KDa) and lane 6 represents pT7-7BBH (49 KDa).

DETAILED DESCRIPTION OF THE INVENTION

Technical Problem

Figure 1:
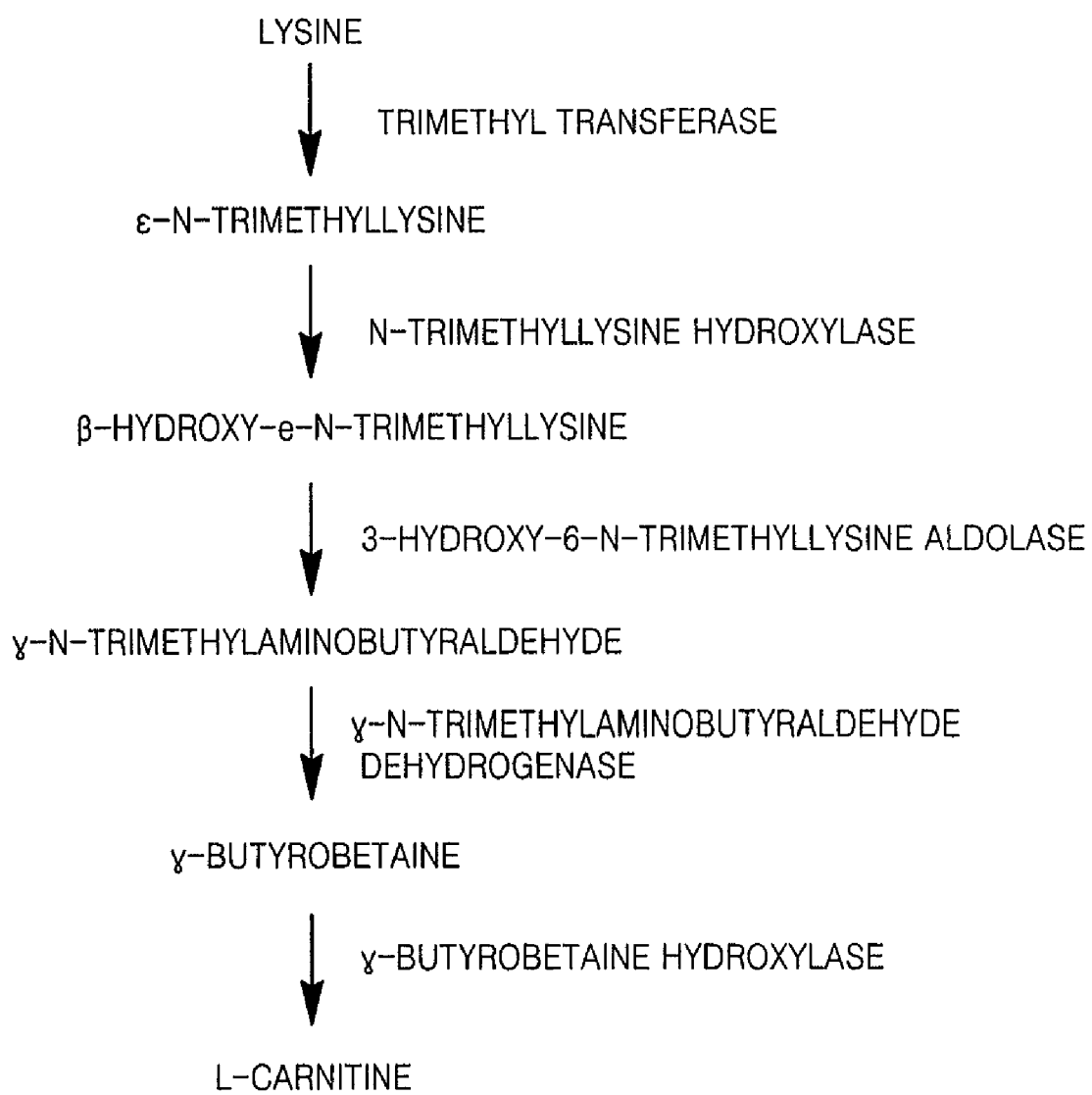
FIG. 1 is a flowchart illustrating a supposed biosynthesis pathway of L-carnitine in *Neurospora crassa*.

The present invention provides a microorganism that can produce L-carnitine at high efficiency The present invention also provides a method of producing L-carnitine using the microorganism.

Technical Solution

According to an aspect of the present invention, there is provided a microorganism that belongs to the *Enterobacteriacae*, the microorganism comprising: polynucleotide encoding activity of S-adenosylmethionine-6-N-lysine methyltransferase (LMT) from *Neurospora crassa*; polynucleotide encoding activity of 3-hydroxy-6-N-trimethyllysine aldolase (TMLA); polynucleotide encoding activity of N-trimethyllysine hydroxylase (TMLH); polynucleotide encoding activity of γ-trimethylaminoaldehyde dehydrogenase (TMABADH); and polynucleotide encoding activity of γ-butyrobetaine hydroxylase (BBH).

The microorganism according to the present invention can be any one including polynucleotide that encodes the five kinds of proteins. Preferably, the microorganism is *Escherichia coli*, and more preferably *Escherichia coli* (Accession number: KCCM-10638)

Polynucleotide that independently encodes five kinds of proteins, that is, LMT, TMLH, TMLA, TMABADH and BBH according to the present invention, can be employed in a microorganism through a vector or by itself. When polynucleotide that independently encodes the five kinds of proteins is employed in a microorganism through a vector, the polynucleotide encoding the five kinds of proteins may be inserted to a single vector and then employed, or may be inserted into at least one vector and then employed. In the present invention, the term "vector" is well-known to those skilled in the art. The vector generally denotes a nucleic acid construct that is used in the introduction of the nucleic acid into a cell. This nucleic acid construct may be a nucleic acid construct derived from a plasmid or a virus genome.

Polynucleotide encoding S-adenosylmethionine-6-N-lysine methyltransferase (LMT) from *Neurospora crassa* according to an embodiment of the present invention encodes S-adenosylmethionine lysinemethyltransferase from *Neurospora crassa*. It is considered that S-adenosylmethionine lysinemethyltransferase catalyzes a reaction of converting lysine into 6-N-trimethyllysine by attaching a methyl group to lysine in a cell of *Neurospora crassa*, but the scope of the present invention is not limited to this specific action mechanism. The polynucleotide encoding S-adenosylmethionine lysinemethyltransferase is preferably polynucleotide encoding an amino acid sequence of SEQ ID NO: 11, and more preferably polynucleotide having a nucleotide sequence of SEQ ID NO: 16.

Polynucleotide encoding N-trimethyllysine hydroxylase (TMLH) from *Neurospora crassa* according to an embodiment of the present invention encodes N-trimethyllysine hydroxylase (TMLH) from *Neurospora crassa*. It is considered that N-trimethyllysine hydroxylase (TMLH) catalyzes a reaction of converting N-trimethyllysine into β-hydroxy-ε-N-trimethyllysine in a cell of *Neurospora crassa*, but the scope of the present invention is not limited to this specific action mechanism. The polynucleotide encoding N-trimethyllysine hydroxylase (TMLH) is preferably polynucleotide encoding an amino acid sequence of SEQ ID NO: 12, and more preferably polynucleotide having a nucleotide sequence of SEQ ID NO: 17.

Polynucleotide encoding 3-hydroxy-6-N-trimethyllysine aldolase (TMLA) from *Neurospora crassa* according to an embodiment of the present invention encodes 3-hydroxy-6-N-trimethyllysine aldolase (TMLA) from *Neurospora crassa*. It is considered that 3-hydroxy-6-N-trimethyllysine aldolase (TMLA) catalyzes a reaction of converting β-hydroxy-ε-N-trimethyllysine into γ-N-trimethylaminobutyraldehyde in a cell of *Neurospora crassa*, but the scope of the present invention is not limited to this specific action mechanism. The polynucleotide encoding 3-hydroxy-6-N-trimethyllysine aldolase (TMLA) is preferably polynucleotide encoding an amino acid sequence of SEQ ID NO: 13, and more preferably polynucleotide having a nucleotide sequence of SEQ ID NO: 18.

Polynucleotide encoding activity of γ-trimethylaminoaldehyde dehydrogenase (TMABADH) from *Neurospora crassa* according to an embodiment of the present invention encodes activity of γ-trimethylaminoaldehyde dehydrogenase (TMABADH) from *Neurospora crassa*. It is considered that γ-trimethylaminoaldehyde dehydrogenase (TMABADH) catalyzes a reaction of converting γ-N-trimethylaminobutyraldehyde into γ-butyrobetaine in a cell of *Neurospora crassa*, but the scope of the present invention is not limited to this specific action mechanism. The polynucleotide encoding γ-trimethylaminoaldehyde dehydrogenase (TMABADH) is preferably polynucleotide encoding an amino acid sequence of SEQ ID NO: 14, and more preferably polynucleotide having a nucleotide sequence of SEQ ID NO: 19.

Polynucleotide encoding activity of γ-butyrobetaine hydroxylase (BBH) from *Neurospora crassa* according to an embodiment of the present invention encodes γ-butyrobetaine hydroxylase (BBH) from *Neurospora crassa*. It is considered that γ-butyrobetaine hydroxylase (BBH) can catalyze a reaction of converting γ-butyrobetaine into L-carnitine in a cell of *Neurospora crassa*, but the scope of the present invention is not limited to this specific action mechanism. The polynucleotide encoding γ-butyrobetaine hydroxylase (BBH) is preferably polynucleotide encoding an amino acid sequence of SEQ ID NO: 15, and more preferably polynucleotide having a nucleotide sequence of SEQ ID NO: 20.

According to another aspect of the present invention, there is provided a method of producing L-carnitine, the method comprising: culturing a microorganism according to the present invention in the presence of a substrate selected from the group consisting of L-lysine, N-trimethyllysine, β-hydroxy-N-trimethyllysine, γ-N-trimethylaminobutyraldehyde, γ-butyrobetaine and mixtures thereof to produce L-carnitine in the culture.

In the method of producing L-carnitine according to the present invention, a concentration of the substrate selected from the group consisting of L-lysine, N-trimethyllysine, β-hydroxy-N-trimethyllysine, γ-N-trimethylaminobutyraldehyde, γ-butyrobetaine and mixtures thereof is preferably 0.1-10 weight % based on the weight of a culture medium, but the present invention is not particularly limited to this range.

In the method according to the present invention, a process of collecting L-carnitine from a culture is well known to those skilled in the art. Examples of such a process include, but are not limited to, ultrafiltration, centrifugal separation, and a method of collecting L-carnitine by recrystallizing the resulting product after cells are separated from a culture such as decantation, and cation exchange chromatography or electrodialysis is performed for the supernatant obtained therefrom.

Advantageous Effects

The microorganism according to the present invention has a good ability of producing L-carnitine so that it can be usefully employed in a method of producing L-carnitine through fermentation.

In the method of producing L-carnitine according to the present invention, L-carnitine can be produced with high efficiency using a microorganism that belongs to the *Enterobacteriacae*.

Best Mode

Hereinafter, the present invention will be described in further detail with reference to the following examples. These examples are for illustrative purposes only and are not intended to limit the scope of the present invention.

EXAMPLE

Polynucleotide encoding five kinds of proteins associated with L-carnitine biosynthesis from L-lysine in *Neurospora crassa*, and a nucleic acid construct including the same were produced. Next, *E. coli* was transformed with the nucleic acid construct, and the transformed *E. coli* was cultured in a medium including an intermediate product obtained throughout a L-carnitine production pathway to produce L-carnitine and collect L-carnitine.

Example 1

Isolation of Polynucleotide Encoding LMT, TMLH, TMLA, TMABADH and BBH from *Neurospora crassa*

Polynucleotide encoding LMT, TMLH, TMLA, TMABADH and BBH from *Neurospora crassa* was isolated and cloned, and a base sequence thereof was analyzed.

(1) Production of cDNA Library of *Neurospora crassa*

The total mRNA was isolated from a culture including fungal body of *Neurospora crassa* (including a sporophyte) and reverse transcribed using poly T as a primer, and then PCR was performed to amplify cDNA. The amplified cDNA was digested with EcoRI and XhoI, and then the digested cDNA was inserted to a site of EcoRI and XhoI of λAD5 cloning vector to produce cDNA library from *Neurospora crassa*.

Next, the cDNA library was infected into *E. coli* BNN322, and then the infected *E. coli* BNN322 was cultured and amplified. First, *E. coli* BNN322 was cultured overnight in a LB medium including 50 μg/ml of kanamycin and 0.2% of maltose. Then, centrifugal separation was performed for the culture obtained therefrom, a supernatant of the resulting product was then removed, and afterwards cell pellets were resuspended in a solution of 1 ml of 10 mM $MgSO_4$. The suspension obtained from the resulting product and $5 \times 10^7$ PFU of the λ cDNA library was incubated at 30° C. for 30 minutes without shaking, and 2 ml of a LB medium was further added to the culture, and then the resulting culture was shaked in a shaking incubator at 30° C. for 1 hour. The cultured cells were streaked on a LB medium plate including ampicillin (75 μg/ml) and incubated at 37° C. for 8 hours. cDNA library pool was separated from colony of the plate using a Wizard kit. λ including the separated cDNA library pool was used as a template to amplify polynucleotide encoding LMT, TMLH, TMLA, TMABADH and BBH.

(2) Amplification and Cloning of Polynucleotide Encoding LMT (an LMT Gene) and Confirmation of LMT Production (a) Isolation of an LMT Gene from *Neurospora crassa* and Confirmation of the Functional Expression of the Gene.

*Neurospora crassa* was cultured and cells were collected. Then, the cells were lysed using 1 M of potassium phosphate buffer pH 7.4 including 2 mM of DTT and 0.2 mM of EDTA, and then protein was extracted. Ammonium sulfate was slowly added to the obtained supernatant to reach a final saturated concentration of 50% to precipitate protein, and then a small amount of 0.1 M of potassium phosphate buffer pH 7.4 was added to the protein precipitated by centrifugation. The resulting solution was desalted using a T1 dialysis membrane and the desalted sample was purified using a DEAE column. At this time, pooling was performed using 0.1 M of potassium phosphate buffer pH 7.4 as a washing buffer and 0.1 M of potassium phosphate buffer pH 7.4 including 0.3 M of NaCl as an eluting buffer. Thereafter, the pooled sample was desalted using a T1 dialysis membrane. The desalted sample was purified by using a CM column. 0.1 M of potassium phosphate buffer pH 7.4 was used as a washing buffer of the column, and a sample that was not adsorbed onto the column and flown out of the column was all pooled.

The protein sample was loaded on the DEAE column again, and then using 0.1 M of potassium phosphate buffer pH 7.4, a concentration gradient elution was performed to reach a NaCl concentration of 0-0.3 M. A protein analysis was performed for the purified sample using natural-PAGE and SDS-PAGE.

Figure 2:
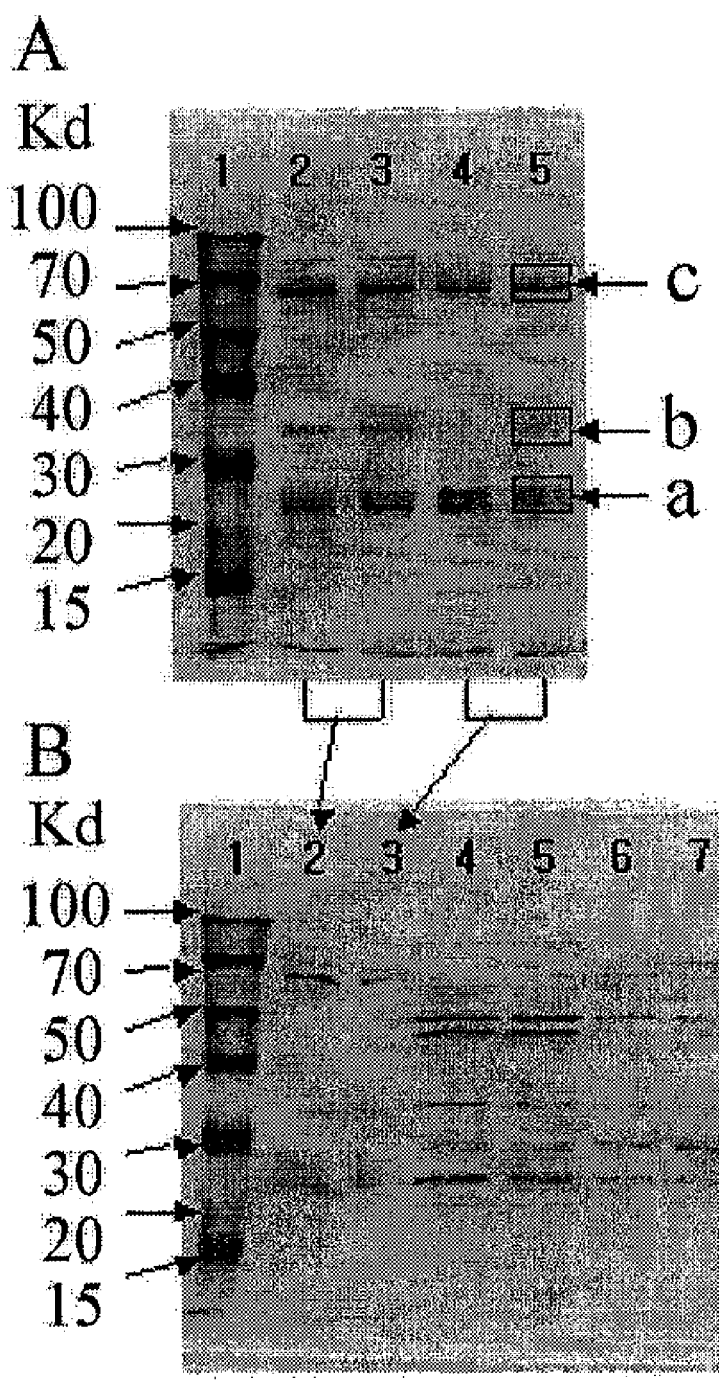
FIG. 2 is a diagram illustrating results of a natural or SDS-PAGE analysis of an eluting solution obtained after a culture of *Neurospora crassa* is lysed and DEAE column chromatography is performed for the lysed material.

FIG. 2 is a diagram illustrating results of a natural-PAGE or SDS-PAGE analysis of an eluting solution obtained after a culture of *Neurospora crassa* was lysed and DEAE column chromatography was performed for the lysed material. In FIG. 2, lane 1 represents a marker, lane 2 and 3 represent results of a natural-PAGE analysis of DEAE eluting peak 2, and lane 4 and 5 represent results of a natural-PAGE analysis of DEAE eluting peak 3. In FIG. 2B, lane 1 represents a marker, lane 2 represents a result of a natural-PAGE analysis of DEAE eluting peak 2, lane 3 represents a result of a natural-PAGE analysis of DEAE eluting peak 3, lane 4 and 5 represent results of a SDS-PAGE analysis of DEAE eluting peak 2, and lane 6 and 7 represent results of a SDS-PAGE analysis of DEAE eluting peak 3.

From the results of FIG. 2, bands of a, b and c were chosen as a LMT candidate protein, and activity of each protein was measured. First, a gel corresponding to each band was cut out, and then the gel was crushed by a homogenizer. Then, 5 ml of 1 g/L lysine (final concentration 500 mg/L) and 2 ml of 1 g/L methyl donor, S-adenosylmethionine (final concentration 200 mg/L) were added thereto and the resulting product was slowly stirred at 28° C. for 24 hours to react, and then a trimethyllysine peak was analyzed using HPLC.

Figure 3:
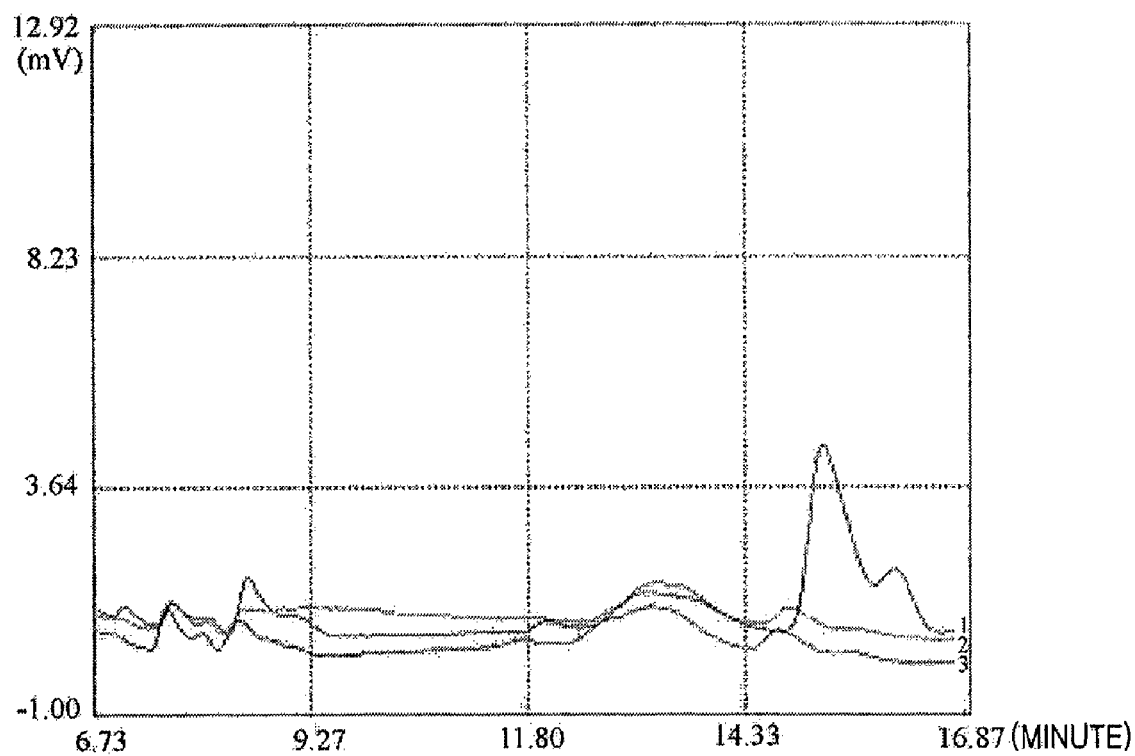
FIG. 3 is a graph illustrating results of measuring trimethyllysine through HPLC after protein bands of a, b and c of FIG. 2 is reacted with lysine and S-adenosylmethionine.

FIG. 3 is a graph representing results of measuring trimethyllysine through HPLC after protein bands of a, b and c are reacted with lysine and S-adenosylmethionine. As illustrated in FIG. 3, in a sample reacted with the band of a, a peak considered as trimethyllysine was confirmed around at a retention time of 15 minutes. In FIGS. 3, 1, 2 and 3 represent results corresponding to each of the bands a, b and c. To exactly confirm the bands, a sample obtained by reacting with the band a was compared with a trimethyllysine standard.

Figure 4:
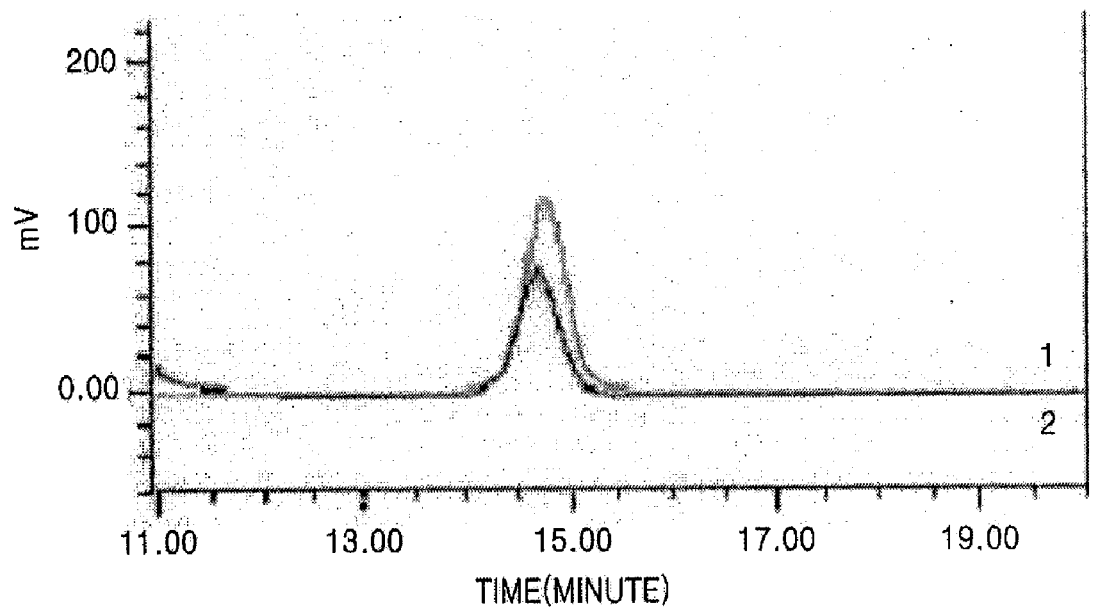
FIG. 4 is a graph showing results of analyzing a sample obtained by reacting with the band of a and a trimethyllysine standard through HPLC.

FIG. 4 is a graph representing results of analyzing a sample obtained by reacting with the protein band of a and trimethyllysine standard through HPLC. As illustrated in FIG. 4, a peak time, a time at which a voltage has the highest value, of the band a is exactly consistent with the standard trimethyllysine sample. Therefore, it is confirmed that the band a includes S-adonosylmethionine-6-N-lysine-methyltransferase, LMT. In FIGS. 4, 1 and 2 refer to results corresponding to each standard and the band a. Each graph of FIGS. 2 and 3 is a graph into which separate HPLC graphs are integrated.

Next, an N-terminal sequence was analyzed to obtain an amino acid sequence of the LMT protein. First, a protein in SDS-PAGE gel was transferred to a PVDF membrane, and then protein bands were cut out to analyze the N-terminal sequence by Edman method. In particular, phenylisothiocyanate (PTC) was reacted with peptide at pH 8-9 and room temperature, and thus the PTC-peptide in which N-terminal was thiocarbamylated was obtained. Thereafter, the PTC-peptide was reacted under acidic condition to separate only N-terminal amino acid therefrom. The separated amino acid was extracted with ethylacetate, identified with HPLC, and analyzed. As a result, it was confirmed that the N-terminal sequence was AFGKL (SEQ ID NO: 21). Like this, a search for entire genome sequence of known *Neurospora crassa* was conducted based on the confirmed N-terminal amino acid sequence. As a result, a protein and a gene having an amino acid sequence that is consistent with the N-terminal sequence of the LMT and a nucleotide sequence were confirmed.

(b) Expression Vector Including a LMT Gene and Production of Microorganism

Figure 5:
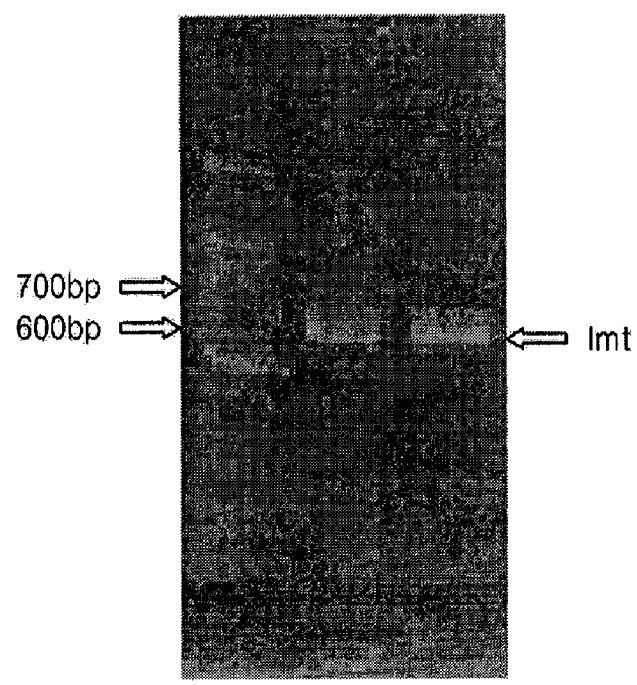
FIG. 5 is a diagram showing electrophoresis results of a LMT gene amplified by PCR.

The cultured *Neurospora crassa* was collected and lysed using a liquid nitrogen, and then RNA was purified using a RNA purification kit. A primer of SEQ ID NOS:1 and 2 was produced using information on an amino acid and base sequence of LMT confirmed in (a), and then, using the cDNA library produced in (1), a gene of S-adonosylmethionine-6-N-lysine-methyltransferase was amplified through PCR that uses the primer set as a primer (FIG. 5). FIG. 5 is a diagram showing electrophoresis results of an LMT gene amplified by PCR.

Figure 6:
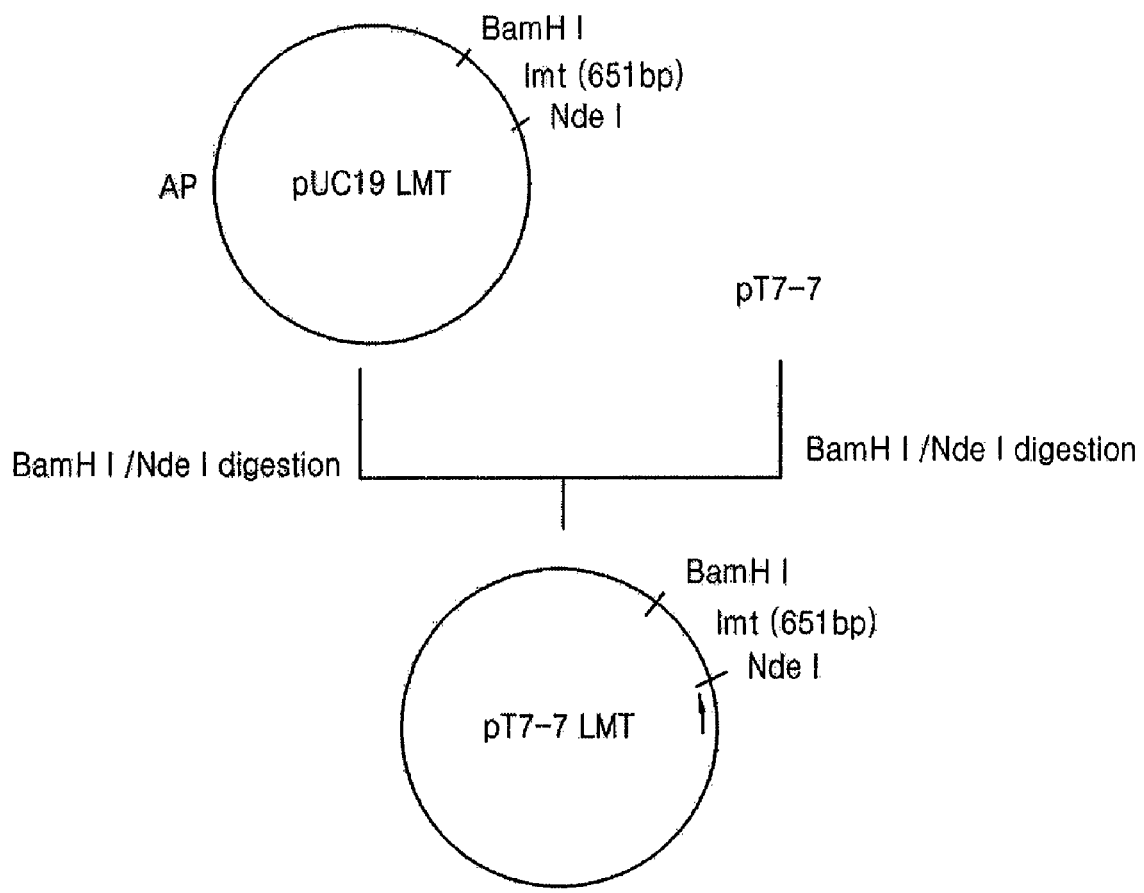
FIG. 6 illustrates a producing process of pT7-7 LMT.

The obtained PCR product and pT7-7 vector were digested with NdeI and BamHI, respectively, and connected to each other with T4 DNA ligase to produce pT7-7 LMT vector (FIG. 6). FIG. 6 illustrates a producing process of pT7-7 LMT. *E. coli* BL21 DE3 was transformed with pT7-7 LMT vector using electroporation. 40 µl of *E. coli* BL21 DE3 and 1 µl of pT7-7-LMT vector were mixed, placed in cold cuvettes with a 2 mm gap, and transformed by electroporation under conditions of 2.5 kV, 200Ω, and 25 µF. The obtained transformant was streaked on a solid plating medium containing ampicillin, and then a plasmid was purified from the transformant selected therefrom and digested with NdeI and BamHI. As a result, the introduction of pT7-7LMT into the plasmid was confirmed by confirming the size of the inserted gene and the plasmid; this was referred to as BL21 (DE3)/pT7-7LMT.

Figure 7:
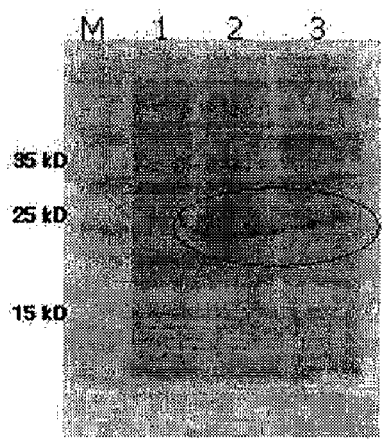
FIG. 7 is a diagram showing results of a SDS-PAGE analysis of supernatant of the lysed bacteria obtained when *E. coli* containing S-adenosysmethionine-6-N-lysine-methyltransferase from *Neurospora crassa* is cultured in the presence of IPTG, and bacteria obtained therefrom is lysed.

(c) Expression of S-adenosylmethionine-6-N-Lysine-Methyltransferase in *E. coli* and Production of Trimethyllysine from Lysine BL21 (DE3)/pT7-7LMT was cultured to $OD_{600}$ 0.5 in a LB medium, and then cultured for more 4 hours after 1 mM of IPTG was added therein. Centrifugation was performed for the culture, and cells were collected and lysed using an ultrasonic wave. By performing SDS-PAGE for the cell lysate, about 25 kD of S-adenosylmethionine-6-N-lysine-methyltransferase was confirmed (FIG. 7). FIG. 7 is a diagram representing results of SDS-PAGE analysis of supernatant obtained when *E. coli* containing S-adenosylmethionine-6-N-lysine-methyltransferase from *Neurospora crassa* was cultured in the presence of IPTG and a microorganism obtained therefrom was lysed. In FIG. 7, lane M refers to a marker, lane 1 refers to a negative control group, lanes 2 and 3 refer to a cell lysate, and a circled part in lane 2 and 3 refers to a band at 25 kD position corresponding to LMT.

*E. coli* BL21(DE3)/pT7-7LMT was cultured to $OD_{600}$ 0.6 in a 250 ml flask equipped with a baffle in which an LB medium including 50 ml of ampicillin was placed, and then cultured at 28° C. for over 8 hours to form an exact tertiary structure of an enzyme and prevent an inclusion body from forming after 1 mM of IPTG was added therein. During culturing, 500 mg/L of L-lysine and 200 mg/L of S— adenosylmethionine were added as a reaction solution, and a trimethyllysine content of a culture solution was measured. The results are shown in Table 1.

Trimethyllysine was measured by HPLC under the following conditions. SUPELCOSIL LC-DABS from Supelco was used as a column. A buffer was made such that 0.1% of trifluoroacetic acid (TFA) was added to a buffer in which a distilled water and acetonitrile were mixed in a ratio of 2:8, and B buffer was made such that 0.1% of TFA was added to a buffer in which a distilled water and acetonitrile were mixed in a ratio of 2:8. Trimethyllysine was analyzed using a linear concentration gradient method, maintaining a flow velocity of 0.8 ml/min.

TABLE 1

| Assayed materials | Trimethyllysine (µg/ml) |
|---|---|
| *E. coli* BL21(DE3)/pT7-7 (IPTG induction) + 500 mg/L lysine + 200 mg/L Ado-Met | 0.0 |
| *E. coli* BL21(DE3)/pT7-7 LMT(IPTG induction) + 500 mg/L lysine + 200 mg/L Ado-Met | 20.0 |

As shown in Table 1, it was confirmed that a gene of S-adenosylmethionine-6-N-lysine-methyltransferase from *Neurospora crassa* was expressed in *E. coli*, and L-lysine was converted into trimethyllysine therefrom.

(3) Amplification and Cloning of Polynucleotide Encoding TMLH (TMLH Gene) and Confirmation of TMLH Production (a) Amplification and Cloning of Polynucleotide Encoding TMLH (TMLH Gene)

PCR was performed using λ including the cDNA library pool of (1) as a template and using SEQ ID NOS: 3 and 4 as a primer. Then, agarose gel electrophoresis was performed for the PCR product obtained. As a result, about 1.4 kb of a desired product was confirmed. The primers of SEQ ID NOS: 3 and 4 include a sequence that is supposed to encode an initiation codon and termination codon of TMLH from *Neurospora crassa*. A potential TMLH from *Neurospora crassa* was searched by conducting a homology search between an amino acid sequence of the total proteins expressed from *Neurospora crassa* genome and an amino acid sequence of known TMLH from humans and rats, the primer of SEQ ID NOS: 3 and 4 were designed from the amino acid sequence of the potential TMLH.

Figure 8:
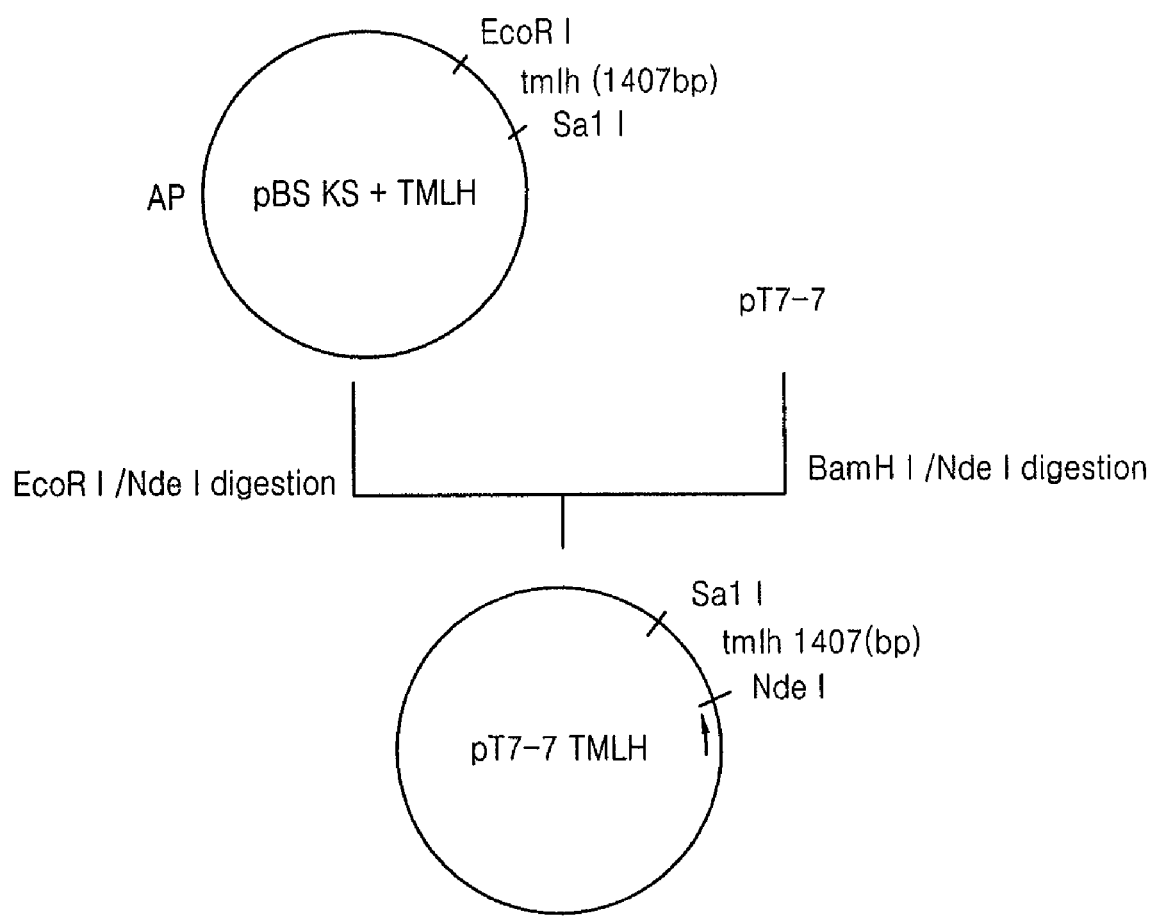
FIG. 8 illustrates a producing process of pT7-7 TMLH.

The PCR product was digested with EcoRI and SalI, and connected to pBS KS+ (Stratagene Inc.) digested with the same enzyme, and then *E. coli* DH5α was transformed with pBS KS+ (TMLH) to which the obtained PCR product was inserted. The transformed *E. coli* DH5α was incubated at 37° C. for 8 hours, and then pBS KS+ (TMLH) was isolated and digested with EcoRI and SalI to determine whether a PCR product was properly inserted. Next, the isolated pBS KS+ (TMLH) was digested with NdeI and SalI, and then a segment of NdeI and SalI was isolated after agarose gel electrophoresis. The segment was connected to expression vector pT7-7 that was digested with the same enzyme to obtain pT7-7 TMLH (refer to FIG. 8). pT7-7 (TMLH) was transformed into the *E. coli* BL21 (DE3).

(b) Confirmation of TMLH Production

Figure 12:
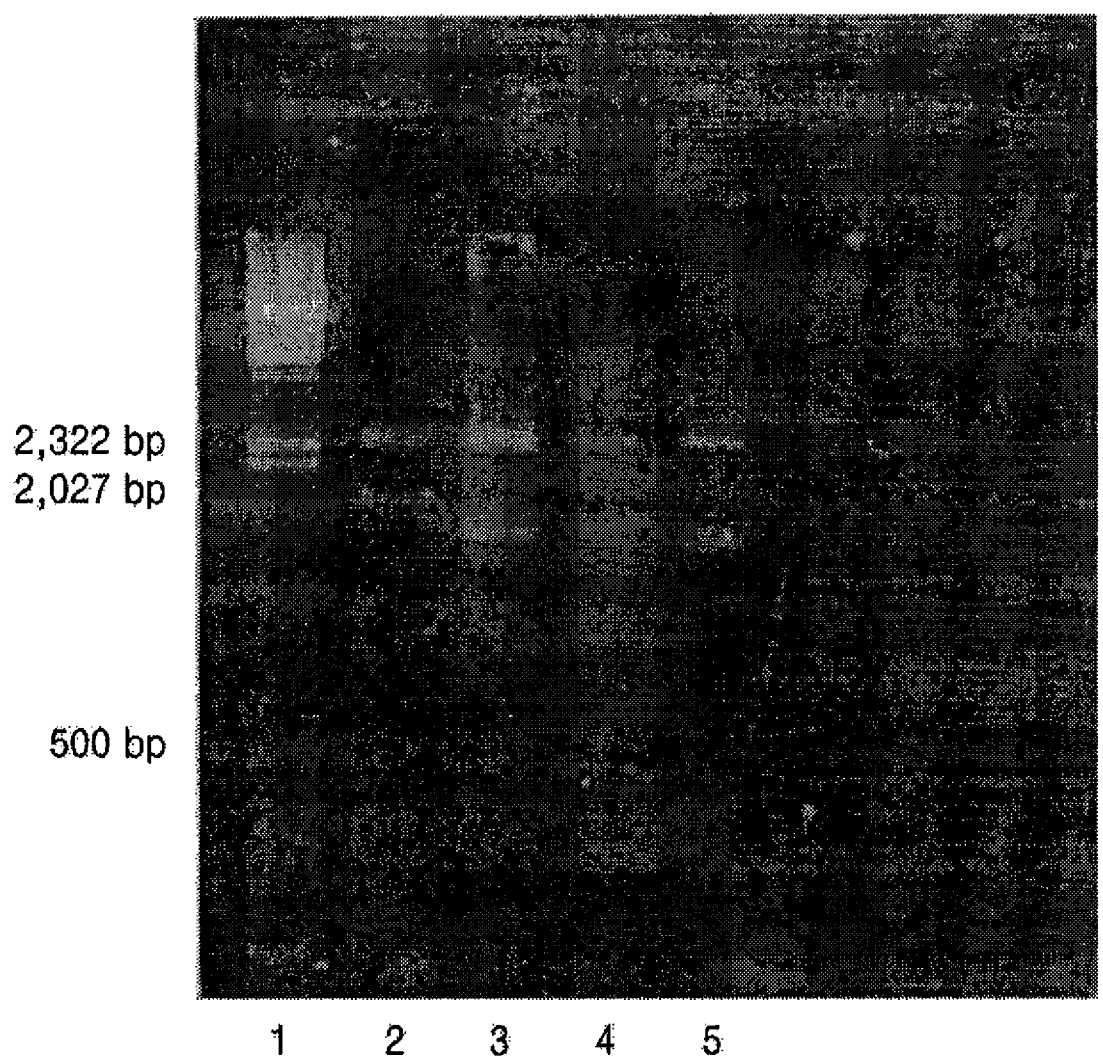
FIG. 12 is a photo showing electrophoresis results of each gene that is inserted onto pT7-7TMLH, pT7-7TMLA, pT7-7TMABADH and pT7-7BBH.

*E. coli* BL21 (DE3) that was transformed with the obtained pT7-7 (TMLH) was incubated to $OD_{600}$ 0.6 at 37° C. in a 250 ml flask equipped with a baffle in which 50 ml of LB medium including 100 µg/ml of ampicillin was placed therein, and incubated for more 4 hours after 1 mM of IPTG was added thereto. pT7-7 (TMLH) was isolated from the culture and digested with NdeI and SalI, and then agarose gel electrophoresis was performed. The results are shown in FIG. 12. As shown in FIG. 12, a band corresponding to a segment of NdeI and SalI was confirmed (lane 2). Next, pT7-7 (TMLH) was isolated and a nucleotide sequence of TMLH was analyzed. As a result, the nucleotide sequence of TMLH was confirmed to be the same sequence as that stored in a database of *Neurospora crassa* genome of NCBI (SEQ ID NO: 17).

Figure 13:
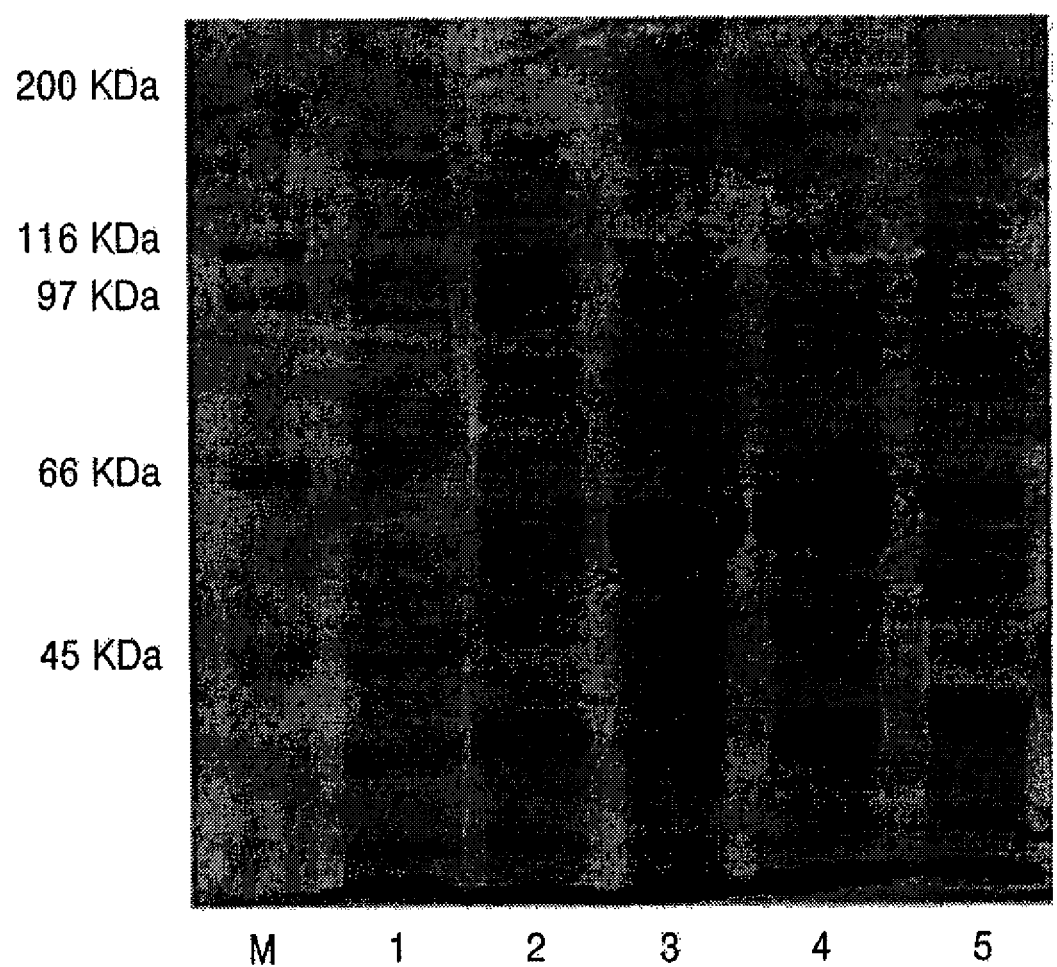
FIG. 13 is a photo showing SDS-PAGE results of a crude extract obtained from the culture of *E. coli* BL21 (DE3) that is transformed with pT7-7TMLH, pT7-7TMLA, pT7-7TMABADH and pT7-7BBH, respectively.

In addition, an expressed TMLH protein was confirmed in cultures of *E. coli* BL21 (DE3) that was transformed with pT7-7 (TMLH). First, centrifugal separation was performed for the culture at 4,000×g for 15 minutes and cell pellets were collected. The obtained cell pellets were added to 1 ml of a lysis buffer (140 mM NaCl, 200 g/l glycerol, and 1 mM DTT in 10 mM of pH 7.4 sodium phosphate buffer solution) and resuspended. The cell suspension was placed in an ice bath and cells were lysed using an ultrasonic disintegrator by propagating an ultrasonic wave five times for 10 seconds each time. Centrifugal separation was performed for the cell lysate with 10,000 g at 4° C. for 20-30 minutes, and then cell debris was removed and the supernatant was collected to obtain a cell crude extract. 8% SDS-PAGE was performed by collecting a sample from the obtained cell crude extract (refer to FIG. 13, lane 2). As a result of performing SDS-PAGE, about 52 KDa of a band corresponding to TMLH was confirmed.

(3) Amplification and Cloning of Polynucleotide Encoding 3-hydroxy-6-N-trimethyllysine aldolase (TMLA) and Confirmation of TMLA Production (a) Amplification and Cloning of Polynucleotide Encoding 3-hydroxy-6-N-trimethyllysine aldolase (TMLA)

PCR was performed using λ including the cDNA library pool of (1) as a template and using SEQ ID NOS: 5 and 6 as a primer. Then, agarose gel electrophoresis was performed for the PCR product obtained. As a result, about 1.4 kb of a desired product was confirmed. The primer of SEQ ID NOS: 5 and 6 included a sequence that encoded an initiation codon and termination codon of TMLA from *Neurospora crassa*. A potential TMLA from *Neurospora crassa* was searched by conducting homology search between an amino acid sequence of total proteins expressed from *Neurospora crassa* genome and an amino acid sequence of known TMLA from humans and rats, the primers SEQ ID NOS: 5 and 6 were designed from the amino acid sequence of the potential TMLA.

Figure 9:
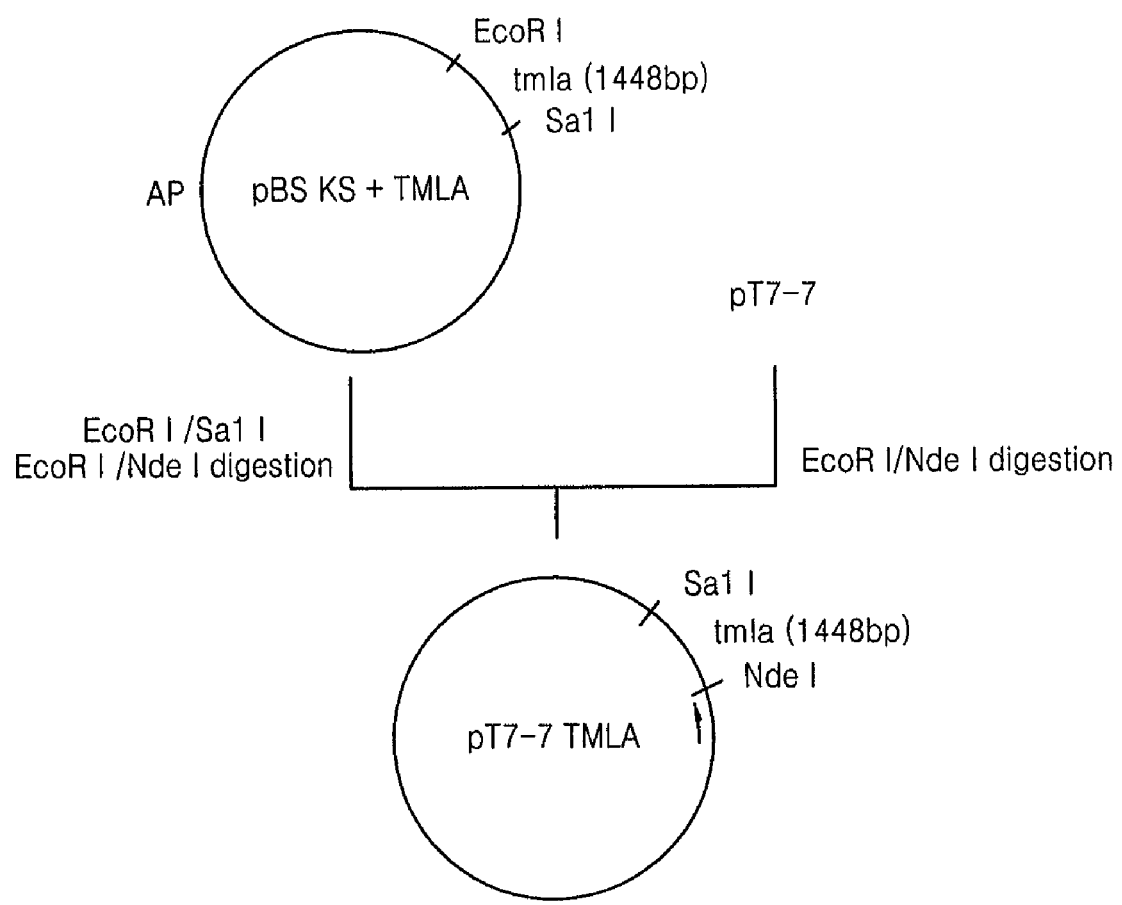
FIG. 9 illustrates a producing process of pT7-7 TMLA.

The PCR product was digested with EcoRI and SalI, and connected to pBS KS+ (Stratagene Inc.) digested with the same enzyme, and then *E. coli* DH5α was transformed with pBS KS+ (TMLA) to which the obtained PCR product was inserted. The transformed *E. coli* DH5α was incubated at 37° C. for 8 hours, and then pBS KS+ (TMLA) was isolated therefrom and digested with EcoRI and SalI to determine whether the PCR product was properly inserted. Next, the isolated pBS KS+ (TMLA) was digested with NdeI and SalI, and then a segment of NdeI and SalI was isolated after agarose gel electrophoresis. The segment was connected to expression vector pT7-7 that was digested with the same enzyme to obtain pT7-7(TMLA) (refer to FIG. 9). *E. coli* BL21 (DE3) was transformed with pT7-7 (TMLA).

(b) Confirmation of TMLA Production

*E. coli* BL21 (DE3) that was transformed with the obtained pT7-7 (TMLA) was incubated to $OD_{600}$ 0.6 at 37° C. in a 250 ml flask equipped with a baffle in which 50 ml of LB medium including 100 μg/ml of ampicillin was placed therein, and then incubated for more 4 hours after 1 mM of IPTG was added thereto. pT7-7 (TMLA) was isolated from the culture and digested with NdeI and SalI, and then agarose gel electrophoresis was performed. The results are shown in FIG. 12. As shown in FIG. 12, a band corresponding to a segment of NdeI and SalI was confirmed (lane 3). Next, pT7-7 (TMLA) was isolated and a nucleotide sequence of TMLA was analyzed. As a result, the nucleotide sequence of TMLA was confirmed to be the same sequence as that stored in a database of *Neurospora crassa* genome of NCBI (SEQ ID NO: 18).

In addition, an expressed TMLA protein was confirmed in cultures of *E. coli* BL21(DE3) that was transformed with pT7-7 (TMLA). First, centrifugal separation was performed for the culture at 4,000×g for 15 minutes and cell pellets were collected. The obtained cell pellets was added to 1 ml of a lysis buffer (140 mM NaCl, 200 g/l glycerol, and 1 mM DTT in 10 mM of sodium phosphate buffer solution pH 7.4) and resuspended. The cell suspension was placed in an ice bath and cells were lysed using an ultrasonic disintegrator by propagating an ultrasonic wave five times for 10 seconds each time. Centrifugal separation was performed for the cell lysate with 10,000 g at 4° C. for 20-30 minutes, and then cell debris was removed and the supernatant was collected to obtain a cell crude extract. 8% SDS-PAGE was performed by collecting a sample from the obtained cell crude extract, (refer to FIG. 13, lane 3). As a result of performing SDS-PAGE, about 53 KDa of a band corresponding to TMLA was confirmed.

(4) Amplification and Cloning of Polynucleotide Encoding γ-trimethylaminoaldehyde Dehydrogenase (TMABADH) and Confirmation of TMABADH Production (a) Amplification and Cloning of Polynucleotide Encoding γ-trimethylaminoaldehyde dehydrogenase (TMABADH)

Figure 10:
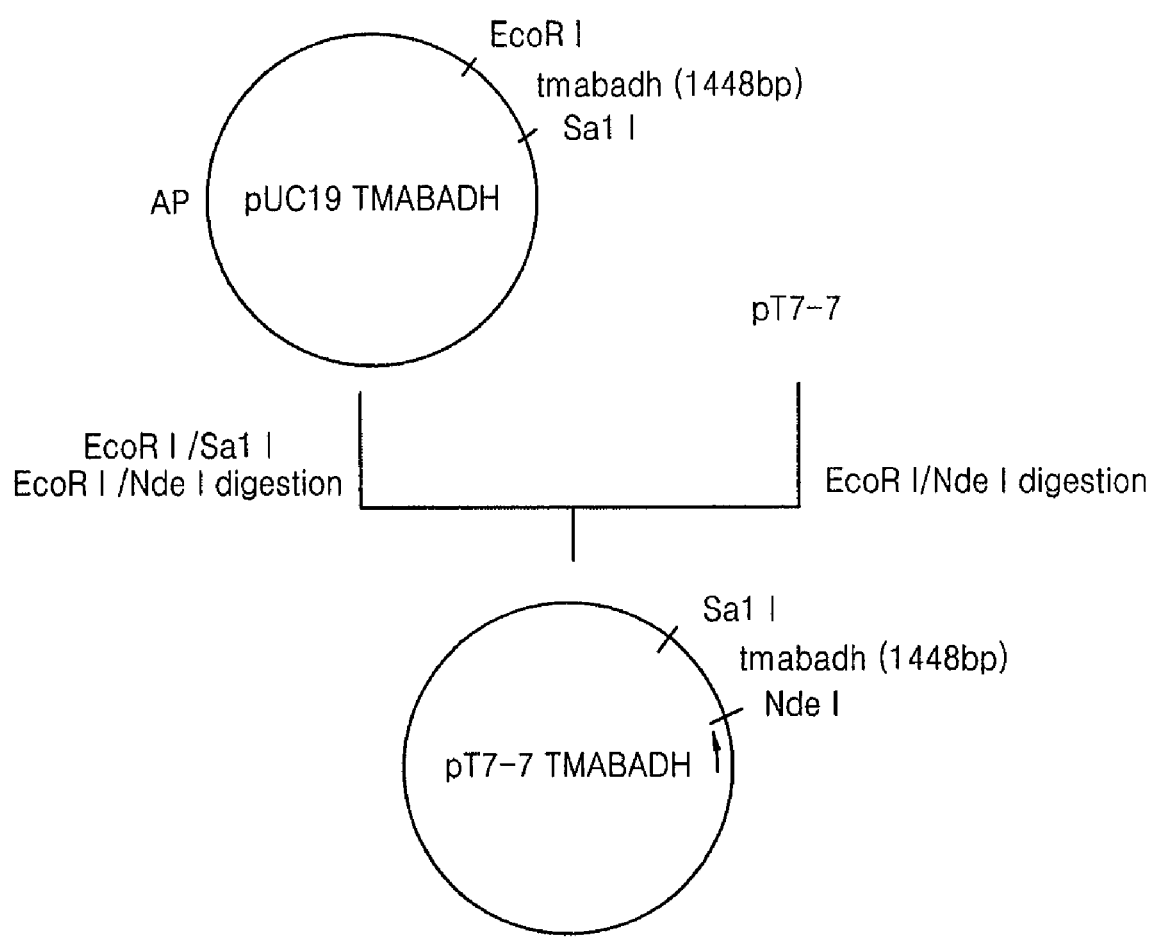
FIG. 10 illustrates a producing process of pT7-7TMABADH.

PCR was performed using A including the cDNA library pool of (1) as a template and using SEQ ID NOS: 7 and 8 as a primer. Then, agarose gel electrophoresis was performed for the PCR product obtained. As a result, about 1.5 kb of a desired product was confirmed. The primer of SEQ ID NOS: 7 and 8 included a sequence that encoded an initiation codon and termination codon of TMABDH from *Neurospora crassa*. A potential TMABADH from *Neurospora crassa* was searched by conducting homology search between an amino acid sequence of total proteins expressed from *Neurospora crassa* genome and an amino acid sequence of known TMABADH from humans and rats, and the primer of SEQ ID NOS: 7 and 8 were designed from the amino acid sequence of the potential TMABADH. The PCR product was digested with EcoRI and SalI, and connected to pBS KS+ (Stratagene Inc.) digested with the same enzyme, and then *E. coli* DH5α was transformed with pBS KS+ (TMABADH) in which the obtained PCR product was inserted. The transformed *E. coli* DH5α was incubated at 37° C. for 8 hours, and then pBS KS+ (TMABADH) was isolated therefrom and digested with EcoRI and SalI to determine whether the PCR product was properly inserted. Next, the isolated pBS KS+ (TMABADH) was digested with NdeI and SalI, and then a segment of NdeI and SalI was isolated after agarose gel electrophoresis. The segment was connected to expression vector pT7-7 that was digested with the same enzyme to obtain pT7-7(TMABADH) (refer to FIG. 10). *E. coli* BL21 (DE3) was transformed with pT7-7 (TMABADH).

(b) Confirmation of TMABADH Production

*E. coli* BL21 (DE3) that was transformed with the obtained pT7-7 (TMABADH) was incubated to $OD_{600}$ 0.6 at 37° C. in a 250 ml flask equipped with a baffle in which 50 ml of LB medium including ampicillin was placed, and then incubated for more 4 hours after 1 mM of IPTG was added thereto. pT7-7 (TMABADH) was isolated from the culture and digested with NdeI and SalI, and then agarose gel electrophoresis was performed. The results are shown in FIG. 12. As shown in FIG. 12, a band corresponding to a segment of NdeI and SalI was confirmed (lane 4). Next, pT7-7 (TMABADH) was isolated and a nucleotide sequence of TMLH was analyzed. As a result, the nucleotide sequence of TMABADH was confirmed to be the same sequence as that stored in a database of *Neurospora crassa* genome of NCBI (SEQ ID NO: 19).

In addition, an expressed TMABADH protein was confirmed in cultures of *E. coli* BL21 (DE3) that was transformed with pT7-7 (TMABADH). First, centrifugal separation was performed for the culture at 4,000×g for 15 minutes and cell pellets were collected. The obtained cell pellets was added to 1 ml of a lysis buffer (140 mM NaCl, 200 g/l glycerol, and 1 mM DTT in 10 mM of sodium phosphate buffer solution pH 7.4) and resuspended. The cell suspension was placed in an ice bath and cells were lysed using an ultrasonic disintegrator by propagating an ultrasonic wave five times for 10 seconds each time. Centrifugal separation was performed for the cell lysate with 10,000 g at 4° C. for 20-30 minutes, and then cell debris was removed and the supernatant was collected to obtain a cell crude extract. 8% SDS-PAGE was performed by collecting a sample from the obtained cell crude extract (refer to FIG. 13). As a result of performing SDS-PAGE, about 55 kD of a band corresponding to TMABADH was confirmed.

(5) Amplification and Cloning of Polynucleotide Encoding γ-Butyrobetaine Hydroxylase (BBH) and Confirmation of BBH Production (a) Amplification and Cloning of Polynucleotide Encoding γ-Butyrobetaine Hydroxylase (BBH)

PCR was performed using λ including the cDNA library pool of (1) as a template and using SEQ ID NOS: 9 and 10 as a primer. Then, agarose gel electrophoresis was performed for the PCR product obtained. As a result, about 1.3 kb of a desired product was confirmed. The primers of SEQ ID NOS: 9 and 10 include a sequence that is supposed to encode an initiation codon and termination codon of BBH from *Neurospora crassa*. A potential BBH from *Neurospora crassa* was searched by conducting homology search between an amino acid sequence of the total proteins expressed from *Neurospora crassa* genome and an amino acid sequence of known BBH from humans and rats, and the primer of SEQ ID NOS: 9 and 10 were designed from the amino acid sequence of the potential BBH.

Figure 11:
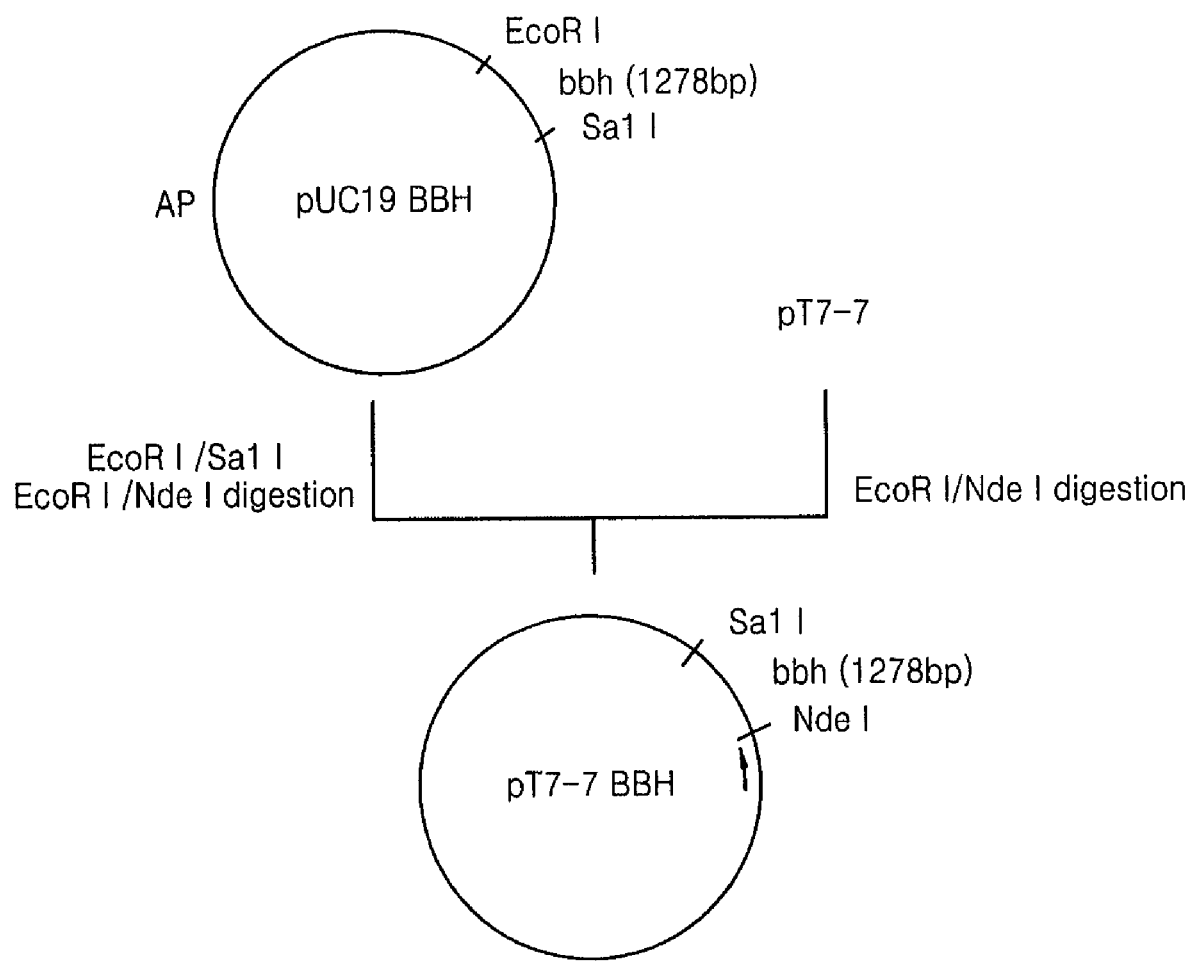
FIG. 11 illustrates a producing process of pT7-7 BBH.

The PCR product was digested with EcoRI and SalI, and connected to pUC19 digested with the same enzyme, and then *E. coli* DH5α was transformed with pUC19 (BBH) to which the obtained PCR product was inserted. The transformed *E. coli* DH5α was incubated at 37° C. for 8 hours in a LB medium including 100 µg/ml of ampicillin and then pUC19 (BBH) was isolated therefrom and digested with EcoRI and SalI to determine whether the PCR product was properly inserted. Next, the isolated pUC19 (BBH) was digested with NdeI and SalI, and then a segment of NdeI and SalI was isolated after agarose gel electrophoresis. The segment was connected to expression vector pT7-7 that was digested with the same enzyme to obtain pT7-7(BBH) (refer to FIG. 11). *E. coli* BL21 (DE3) was transformed with pT7-7 (BBH).

*E. coli* BL21 (DE3) that was transformed with the obtained pT7-7 (BBH) was incubated to $OD_{600}$ 0.6 at 37° C. in a 250 ml flask equipped with a baffle in which 50 ml of LB medium including 100 µg/ml of ampicillin was placed therein, and then incubated for more 4 hours after 1 mM of IPTG was added thereto. pT7-7 (BBH) was isolated from the culture and digested with NdeI and SalI, and then 0.8% agarose gel electrophoresis was performed. The results are shown in FIG. 12. As shown in FIG. 12, a band corresponding to a segment of NdeI and SalI was confirmed (lane 5). Next, pT7-7 (BBH) was isolated and a nucleotide sequence of BBH was analyzed. As a result, the nucleotide sequence of BBH was confirmed to be the same sequence as that stored in a database of *Neurospora crassa* genome of NCBI (SEQ ID NO: 20).

(b) Confirmation of Production of BBH Protein

An expressed BBH protein was confirmed in cultures of *E. coli* BL21(DE3) that was transformed with pT7-7 (BBH). First, centrifugal separation was performed for the culture at 4,000×g for 15 minutes and cell pellets were collected. The obtained cell pellets was added to 1 ml of a lysis buffer (140 mM NaCl, 200 g/l glycerol, and 1 mM DTT in 10 mM of sodium phosphate buffer solution pH 7.4) and resuspended. The cell suspension was placed in an ice bath and cells were lysed using an ultrasonic disintegrator by propagating an ultrasonic wave five times for 10 seconds each time. Centrifugal separation was performed for the cell lysate with 10,000 g at 4° C. for 20-30 minutes, and then cell debris was removed and the supernatant was collected to obtain a cell crude extract. 8% SDS-PAGE was performed by collecting a sample from the obtained cell crude extract, (refer to FIG. 13, lane 5). As a result of performing SDS-PAGE, about 49 kDa of a band corresponding to BBH was confirmed.

Example 2

Production of Host Cell Including all of LMT, TMLH, TMLA, TMABADH and BBH Gene

Genes of LMT, TMLH and BBH from cDNA library of *Neurospora crassa* that was produced in Example 1 were amplified, and pT7-7 ABE having all of the three genes was produced. In addition, genes of TMLA and TMABADH from cDNA library of *Neurospora crassa* that was produced in Example 1 were produced, and pACYC184-CarCD having all of the two genes was produced. The produced pT7-7-CarABE and pACYC184-CarCD were employed in *E. coli* to produce a transformed microorganism having all of the genes of LMT, TMLH, TMLA, TMABADH and BBH. The transformed microorganism was referred to as *E. coli* BL21 (DE3) CJ2004-2, and deposited on Dec. 13, 2004, in Korean Culture Center of Microorganisms (KCCM), an International Depositary Authority (Accession number KCCM-10638).

Figure 14:
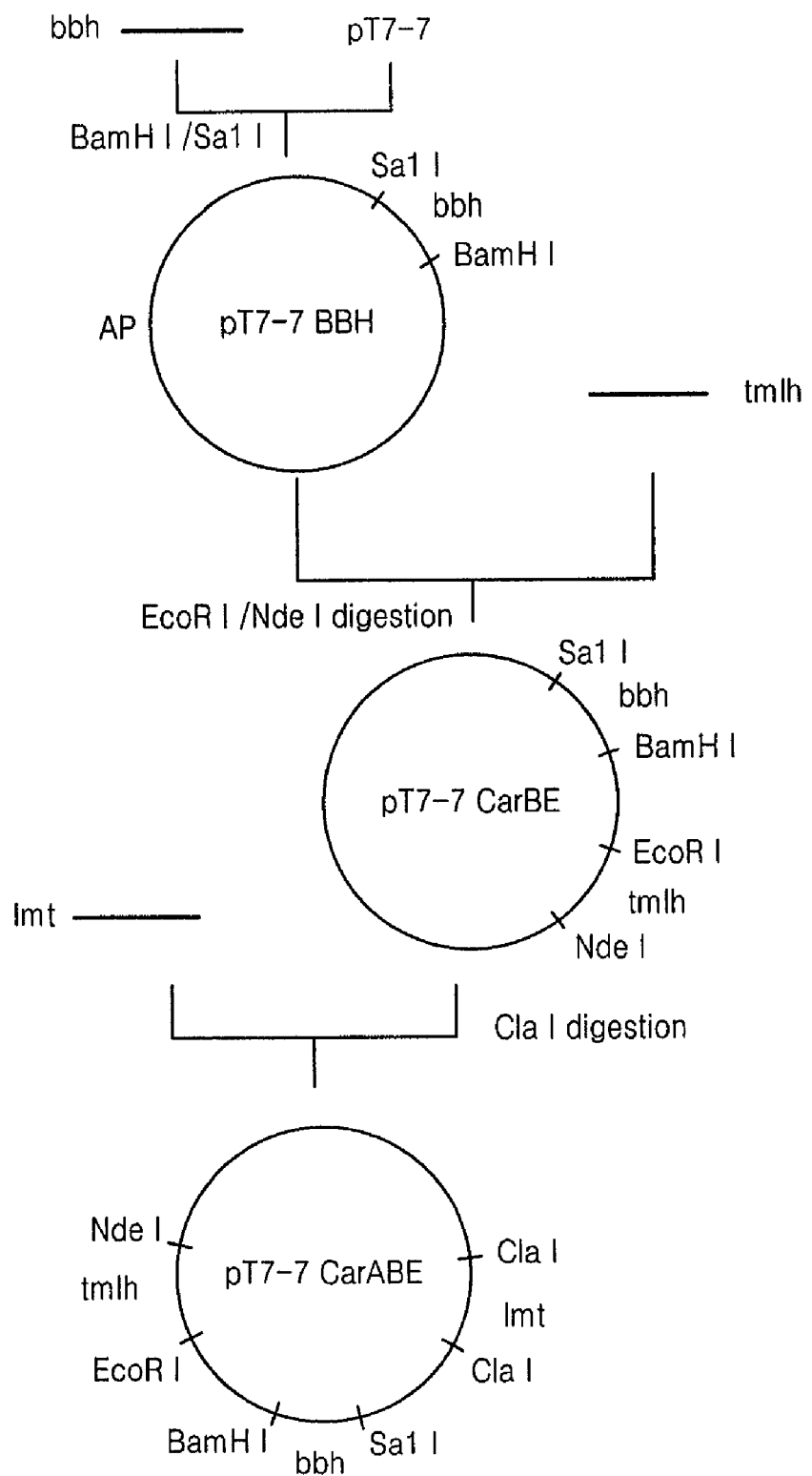
FIG. 14 illustrates a producing process of pT7-7CarABE.
Figure 15:
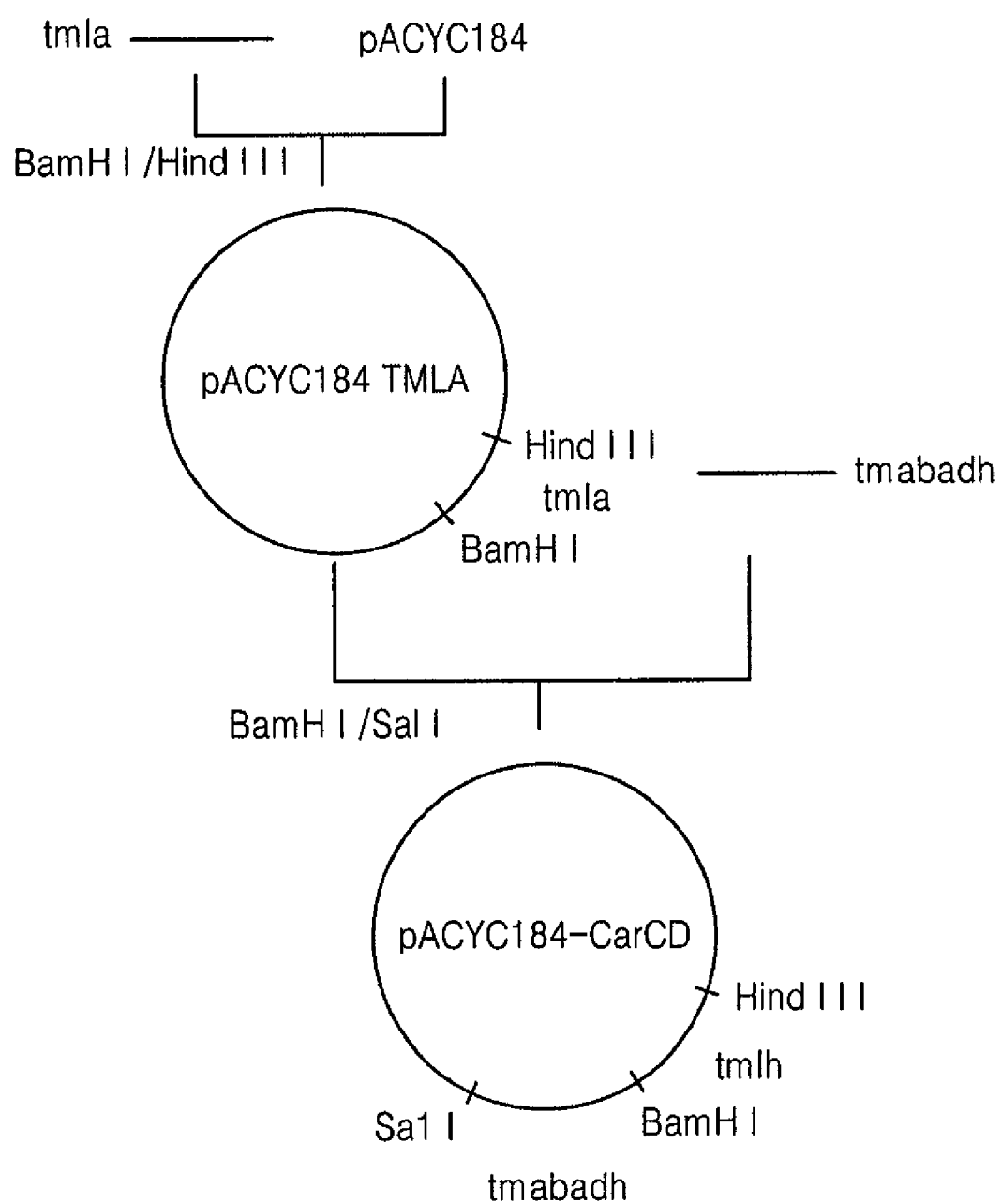
FIG. 15 illustrates a producing process of pACYC184CarCD.

(1) Production of pT7-7-CarABE Having all of the Three Genes of LMT, TMLH and BBH First, lmt including termination codon was amplified from T7 promoter using cDNA library of *Neurospora crassa* as a template and using oligonucleotide of SEQ ID NOS: 1 and 2 as a primer. Next, TMLH including termination codon was amplified from T7 promoter using cDNA library of *Neurospora crassa* as a template and using oligonucleotide of SEQ ID NOS: 3 and 4 as a primer. Then, BBH including termination codon was amplified from T7 promoter using oligonucleotide of SEQ ID NOS: 9 and 10 as a primer. The amplified product of LMT, TMLH and BBH was introduced into pT7-7. First, the amplified product of BBH was digested with a restriction enzyme, such as BamHI and SalI, and segments of BamHI and SalI were obtained therefrom, and then the segments were connected to pT7-7 that was digested with the same enzyme to obtain pT7-7 BBH. Next, the amplified product of TMLH was digested with NdeI and EcoRI, and segments of NdeI and EcoRI were obtained therefrom, and then the segments were connected to pT7-7 BBH that was digested with the same enzyme to obtain pT7-7 CarBE. Then, the amplified product of LMT was digested with ClaI, and a segment of ClaI was obtained therefrom, and then the segment was connected to lmt that was digested with the same enzyme to obtain pT7-7 CarABE (refer to FIG. 14).

(2) Production of pACYC184 CarCD Having all of the Genes of TMLA and TMABADH

First, TMLA including termination codon was amplified from T7 promoter using cDNA library of *Neurospora crassa* as a template and using oligonucleotide of SEQ ID NOS: 5 and 6 as a primer. Next, TMABADH including termination codon was amplified from T7 promoter using cDNA library of *Neurospora crassa* as a template and using oligonucleotide of SEQ ID NOS: 7 and 8 as a primer. The amplified products of TMLA and TMABADH were introduced into pACYC184. First, the amplified product of TMLA was digested with BamHI and HIndIII, and segments of BamHI and HindIII were obtained therefrom, and then the segments were connected to pACYC184 that was digested with the same enzyme to obtain pACYC184 TMLA. Next, the amplified product of TMABADH was digested with BamHI and SalI, and segments of BamHI and SalI were obtained therefrom, and then the segments were connected to pACYC184 TMLA that was digested with the same enzyme to obtain pACYC184 CarCD.

Example 3

Production of L-Carnitine Using a Microorganism Including Polynucleotide Encoding LMT, TMLH, TMLA, TMABADH and BBH

*E. coli* BL21(DE3) in which both pT7-7-CarABE and pACYC184-CarCD produced in Example 2 were introduced was cultured in a medium including L-lysine, and a production amount of L-carnitine was determined. The introduction of pT7-7-CarABE and pACYC184-CarCD into *E. coli* BL21 (DE3) was performed using electroporation as described in Example 1.

(1) Production of L-Carnitine by Culturing *E. coli* BL21 (DE3) that was Transformed with Both PT7-7-CarABE and pACYC184-CarCD that were Produced in Example 2

First, *E. coli* BL21 (DE3) that was transformed with both pT7-7-CarABE and pACYC184-CarCD was plated in a LB solid plating medium including ampicillin (100 μg/ml) and chloramphenicol (50 μg/ml), and cultured. Colonies of the microorganism in the solid plating medium were incubated to $OD_{600}$ 1.0 at 37° C. for 12 hours in a flask including 20 ml of a LB medium to which ampicillin (100 μg/ml) and chloramphenicol (50 μg/ml) were added. 0.1 ml of a culture of the incubated microorganism was placed in a 250 ml flask equipped with a baffle including 20 ml of a LB medium that has 2 mM of L-lysine, and then incubated to $OD_{600}$ 0.6 at 37° C. When IPTG was added, 1 mM of IPTG was added after a value of $OD_{600}$ reached 0.6 and then the microorganism was incubated for more 4 hours. A group of incubating the microorganism in a LB medium without L-lysine that was induced with IPTG using the same method described above and group of culturing the microorganism in a LB medium including L-lysine that was not induced with IPTG were used as a control group. After incubation was terminated, a L-carnitine content of the culture was determined using in the same manner as in (1). The results are shown in Table 2.

TABLE 2

| Production of L-carnitine by single culture | |
|---|---|
| Culture condition | Concentration (mg/l) |
| LB medium(IPTG induction) | 0 |
| 2 mM LB medium including lysine(IPTG no induction) | 0.14 |
| 2 mM LB medium including lysine(IPTG induction) | 19.81 |

As shown in Table 2, by culturing a microorganism including all of the polynucleotides encoding LMT, TMLH, TMLA, TMABADH and BBH in a medium containing L-lysine, L-carnitine can be produced at high efficiency. In addition, production amounts of L-carnitine shown in Table 2 were compared to one another, and it was confirmed that L-carnitine has higher producing efficiency when cultured in a medium including lysine.

The invention claimed is:

1. A transformed microorganism that belongs to the *Enterobacteriacae* genus, the microorganism comprising:
    a polynucleotide encoding a polypeptide having S-adenosylmethionine-6-N-lysine methyltransferase activity from *Neurospora crassa*, wherein the polynucleotide is a polynucleotide encoding the amino acid sequence of SEQ ID NO: 11;
    a polynucleotide encoding a polypeptide having 6-N-trimethyllysine hydroxylase activity wherein the polynucleotide is a polynucleotide encoding the amino acid sequence of SEQ ID NO: 12;
    a polynucleotide encoding a polypeptide having 3-hydroxy-6-N-trimethyllysine aldolase activity wherein the polynucleotide is a polynucleotide encoding the amino acid sequence of SEQ ID NO: 13;
    a polynucleotide encoding a polypeptide having γ-trimethylaminoaldehyde dehydrogenase activity wherein the polynucleotide is a polynucleotide encoding the amino acid sequence of SEQ ID NO: 14, and
    a polynucleotide encoding a polypeptide having γ-butyrobetaine hydroxylase activity wherein the polynucleotide is a polynucleotide encoding the amino acid sequence of SEQ ID NO: 15.

2. The microorganism of claim 1, wherein the microorganism is *Escherichia coli*.

3. The microorganism of claim 1, wherein the microorganism is *Escherichia coli* (accession number: KCCM-10638).

4. A method of producing L-carnitine, the method comprising:
    culturing a microorganism according to claim 1 in the presence of a substrate selected from the group consisting of L-lysine, N-trimethyllysine, β-hydroxy-N-trimethyllysine, γ-N-trimethylaminobutyraldehyde, γ-butyrobetaine and mixtures thereof to produce L-carnitine in the culture.

5. The method of claim 4, wherein the concentration of the substrate selected from the group consisting of L-lysine, N-trimethyllysine, β-hydroxy-N-trimethyllysine, γ-N-trimethylaminobutyraldehyde, γ-butyrobetaine and mixtures thereof is 0.1-10 weight % based on the weight of a culture medium.

* * * * *